United States Patent
Plott et al.

(10) Patent No.: US 12,370,297 B2
(45) Date of Patent: *Jul. 29, 2025

(54) DEVICES AND METHODS FOR EXTRACORPOREAL CONDITIONING OF BLOOD

(71) Applicant: Michigan Critical Care Consultants, Inc., Dexter, MI (US)

(72) Inventors: Christopher J Plott, Dexter, MI (US); Robert L Beane, III, Ann Arbor, MI (US)

(73) Assignee: Michigan Critical Care Consultants, Inc., Dexter, MI (US)

( * ) Notice: Subject to any disclaimer, the term of this patent is extended or adjusted under 35 U.S.C. 154(b) by 1305 days.

This patent is subject to a terminal disclaimer.

(21) Appl. No.: 16/983,110

(22) Filed: Aug. 3, 2020

(65) Prior Publication Data

US 2020/0360591 A1    Nov. 19, 2020

Related U.S. Application Data

(63) Continuation of application No. 15/712,773, filed on Sep. 22, 2017, now Pat. No. 10,898,633.

(Continued)

(51) Int. Cl.
*A61M 1/36*    (2006.01)
*A61M 1/16*    (2006.01)
(Continued)

(52) U.S. Cl.
CPC ........ *A61M 1/3627* (2013.01); *A61M 1/1698* (2013.01); *A61M 1/3623* (2022.05);
(Continued)

(58) Field of Classification Search
CPC .............. A61M 1/3629; A61M 1/3623; A61M 1/1698; A61M 1/3639; A61M 1/3653;
(Continued)

(56) References Cited

U.S. PATENT DOCUMENTS 4,239,729 A    12/1980    Hasegawa et al.
4,959,152 A     9/1990    Nichols
(Continued)

FOREIGN PATENT DOCUMENTS

CN    101312758 A    11/2008
CN    101610801 A    12/2009
(Continued)

OTHER PUBLICATIONS

Communication pursuant to Article 94(3) EPC from counterpart European Application No. 17781245.0 dated Sep. 7, 2023, 6 pp.

(Continued)

*Primary Examiner* — Philip R Wiest
(74) *Attorney, Agent, or Firm* — Shumaker & Sieffert, P.A.

(57) ABSTRACT

The disclosure relates to devices and methods for extracorporeal conditioning of blood. Extracorporeal blood oxygenators and blood oxygenator components, such as conditioning modules, are described. An extracorporeal blood oxygenator includes a conditioning module having an external frame, an inlet cover, an outlet cover, and an internal chamber. A fiber assembly is disposed within the internal chamber and a potting material on the fiber assembly creates a circumferential seal that defines a passageway through the fiber assembly having a substantially circular cross-sectional shape. A fluid inlet is in fluid communication with the passageway, has a lumen that extends along an axis that is substantially perpendicular to the fiber assembly, and has an internal curvilinear surface adjacent the fiber assembly. A fluid outlet on the opposite side of the fiber assembly also has a lumen that extends along an axis that is substantially perpendicular to the fiber assembly.

26 Claims, 16 Drawing Sheets

Related U.S. Application Data

(60) Provisional application No. 62/486,182, filed on Apr. 17, 2017, provisional application No. 62/397,996, filed on Sep. 22, 2016.

(51) Int. Cl.
  *B01D 19/00* (2006.01)
  *B01D 61/28* (2006.01)
  *B01D 63/02* (2006.01)

(52) U.S. Cl.
  CPC ..... *B01D 19/0031* (2013.01); *B01D 19/0042* (2013.01); *B01D 19/0057* (2013.01); *B01D 61/28* (2013.01); *B01D 63/031* (2022.08); *B01D 63/033* (2022.08); *A61M 1/3639* (2013.01); *A61M 1/3653* (2013.01); *A61M 2205/127* (2013.01); *B01D 2313/08* (2013.01); *B01D 2313/10* (2013.01); *B01D 2313/201* (2022.08)

(58) Field of Classification Search
  CPC . A61M 2205/127; B01D 63/31; B01D 63/33; B01D 19/0031; B01D 19/0042; B01D 19/0057; B01D 61/28; B01D 2312/08; B01D 2312/10
  See application file for complete search history.

(56) References Cited

U.S. PATENT DOCUMENTS

| | | |
|---|---|---|
| 5,162,101 A | 11/1992 | Cosentino |
| 5,174,900 A | 12/1992 | Nichols et al. |
| 5,665,061 A | 9/1997 | Antwiler |
| 5,690,831 A | 11/1997 | Kenley et al. |
| 5,753,173 A | 5/1998 | Leonard et al. |
| 5,817,279 A | 10/1998 | Eilers et al. |
| 5,965,089 A | 10/1999 | Jarvik et al. |
| 6,017,493 A | 1/2000 | Cambron et al. |
| 6,117,390 A | 9/2000 | Corey, Jr. |
| 6,451,257 B1 | 9/2002 | Flamer |
| 6,589,482 B1 | 7/2003 | Burbank et al. |
| 6,730,267 B2 | 5/2004 | Stringer et al. |
| 6,773,670 B2 | 8/2004 | Stringer et al. |
| 7,175,809 B2 | 2/2007 | Gelfand et al. |
| 7,189,352 B2 | 3/2007 | Carpenter et al. |
| 7,198,751 B2 | 4/2007 | Carpenter et al. |
| 7,455,812 B2 | 11/2008 | Thomas |
| 7,470,396 B2 | 12/2008 | Meiser et al. |
| 7,541,000 B2 | 6/2009 | Stringer et al. |
| 7,630,078 B1 | 12/2009 | Nabutovsky et al. |
| 7,641,795 B2 | 1/2010 | Taylor et al. |
| 7,660,616 B1 | 2/2010 | Poore |
| 7,840,246 B1 | 11/2010 | Poore |
| 7,871,566 B2 | 1/2011 | Strauss et al. |
| 8,038,640 B2 | 10/2011 | Orr |
| 8,057,419 B2 | 11/2011 | Ellingboe et al. |
| 8,133,195 B2 | 3/2012 | Blicke et al. |
| 8,175,668 B1 | 5/2012 | Nabutovsky et al. |
| 8,187,216 B2 | 5/2012 | Niitsuma |
| 8,320,981 B1 | 11/2012 | Mayer et al. |
| 8,444,586 B2 | 5/2013 | Beck |
| 8,545,754 B2 | 10/2013 | Carpenter et al. |
| 8,708,986 B2 | 4/2014 | Shapland et al. |
| 8,709,343 B2 | 4/2014 | Thomas |
| 8,747,742 B2 | 6/2014 | Kawamura et al. |
| 8,795,220 B2 | 8/2014 | Reggiani et al. |
| 8,795,591 B2 | 8/2014 | Roller et al. |
| 8,858,485 B2 | 10/2014 | Neri et al. |
| 8,864,700 B2 | 10/2014 | Kawamura et al. |
| 8,888,730 B2 | 11/2014 | Rossi et al. |
| 9,132,214 B2 | 9/2015 | Rossi et al. |
| 9,192,709 B2 | 11/2015 | Fontanazzi et al. |
| 9,199,025 B2 | 12/2015 | Mizoguchi et al. |
| 9,211,371 B2 | 12/2015 | Thomas |
| 9,320,844 B2 | 4/2016 | Joost et al. |
| 9,328,044 B2 | 4/2016 | Joost et al. |
| 9,393,357 B2 | 7/2016 | Ellingboe et al. |
| 9,408,960 B2 | 8/2016 | McLevish |
| 9,421,328 B2 | 8/2016 | Brueckner et al. |
| 10,286,137 B2 | 5/2019 | Maurer et al. |
| 10,610,629 B2 | 4/2020 | Matheis et al. |
| 10,898,633 B2 * | 1/2021 | Plott .................... B01D 61/28 |
| 10,898,663 B2 | 1/2021 | Bothma |
| 2007/0278145 A1 | 12/2007 | Taylor et al. |
| 2010/0274170 A1 | 10/2010 | Carpenter et al. |
| 2012/0190103 A1 | 7/2012 | Maurer |
| 2012/0193289 A1 | 8/2012 | Cloutier et al. |
| 2012/0277653 A1 | 11/2012 | Olsen et al. |
| 2013/0043177 A1 | 2/2013 | Taylor et al. |
| 2014/0061116 A1 | 3/2014 | Schmitz-Rode et al. |
| 2016/0095969 A1 * | 4/2016 | Maurer ................. A61M 1/262 264/263 |
| 2018/0117231 A1 | 5/2018 | Matheis et al. |

FOREIGN PATENT DOCUMENTS

| | | |
|---|---|---|
| CN | 101121099 B | 6/2010 |
| CN | 202459508 U | 3/2012 |
| CN | 103491992 A | 1/2014 |
| CN | 105377404 A | 3/2016 |
| DE | 4308850 A1 | 9/1994 |
| EP | 0521495 A2 | 1/1993 |
| EP | 1864709 B1 | 12/2007 |
| EP | 1941919 A1 | 7/2008 |
| GB | 2063108 A | 9/1980 |
| JP | S6171136 U | 5/1986 |
| JP | 2007143614 A | 6/2007 |
| JP | 2012524626 A | 10/2012 |
| JP | 2016518209 A | 6/2016 |
| WO | 1999049913 A1 | 10/1999 |
| WO | 2002071039 A1 | 9/2002 |
| WO | 2010124087 A1 | 10/2010 |
| WO | 2014183852 A1 | 11/2014 |

OTHER PUBLICATIONS

Decision to Grant, and machine translation thereof, from counterpart Japanese Application No. 2019537749 dated Mar. 23, 2022, 5 pp.
First Office Action and Search Report, and machine translation thereof, from counterpart Chinese Application No. 201780067790.7 dated Apr. 2, 2021, 21 pp.
International Preliminary Report on Patentability from International Application No. PCT/US2017/052960 dated Mar. 26, 2019, 8 pp.
International Search Report and Written Opinion of International Application No. PCT/US2017/052960 dated Dec. 12, 2017, 11 pp.
Notice of Intent to Grant, and machine translation thereof, from counterpart Chinese Application No. 201780067790.7 dated Jan. 24, 2022, 3 pp.
Notification of Reason for Refusal, and machine translation thereof, from counterpart Japanese Application No. 2019537749 dated Jun. 30, 2021, 8 pp.
Prosecution History from U.S. Appl. No. 15/712,773, now issued U.S. Pat. No. 10,898,663, dated Mar. 20, 2019 through Sep. 18, 2020, 115 pp.
Response to Communication pursuant to Article 94(3) EPC dated Sep. 7, 2023, from counterpart European Application No. 17781245.0 filed Jan. 11, 2024, 15 pp.
Response to Communication Pursuant to Rules 161(1) and 162 EPC dated May 8, 2019, from counterpart European Application No. 17781245.0, filed Nov. 18, 2019, 19 pp.

* cited by examiner

DEVICES AND METHODS FOR EXTRACORPOREAL CONDITIONING OF BLOOD

RELATED APPLICATIONS

This application is a continuation of U.S. application Ser. No. 15/712,773, filed on Sep. 22, 2017 and which claims the benefits of U.S. provisional application 62/397,996, filed on Sep. 22, 2016, and U.S. provisional application 62/486,182, filed on Apr. 17, 2017. Each of these related applications is hereby incorporated into this disclosure in its entirety.

FIELD

The disclosure relates to the field of devices for extracorporeal conditioning of blood and components of devices for extracorporeal conditioning of blood. More particularly, the disclosure relates to extracorporeal blood oxygenators and blood oxygenator components, such as conditioning modules. Particular embodiments relate to extracorporeal blood oxygenators that include an integrated heat exchanger. The disclosure also relates to methods of manufacturing devices for extracorporeal conditioning of blood and to methods of manufacturing components of devices for extracorporeal conditioning of blood.

BACKGROUND

Current designs for devices useful for the extracorporeal conditioning of blood typically include one or more sets of mats that each comprise a plurality of hollow fibers. The mats are arranged in a stack and a potting material is used to secure the mats to each other. The potting material defines an internal chamber that extends through the inner portion of the stack of mats. The ends of the hollow fibers are positioned along the outer perimeter of the stack and remain open. A fluid, such as a heat or gas exchange fluid, can be passed through the hollow fibers while blood is directed through the chamber. The blood is conditioned as it moves across the individual fibers, responding to the particular fluid passing through the fibers in the mats.

While devices that conform to this typical design have proven useful and effective, they have many drawbacks. A need exists, therefore, for improved devices for extracorporeal conditioning of blood and for improved methods of manufacturing devices for extracorporeal conditioning of blood and of manufacturing components of such devices.

BRIEF SUMMARY OF SELECTED EXAMPLES

Various example devices for extracorporeal conditioning of blood are described.

An example device for extracorporeal conditioning of blood comprises a housing and a fluid inlet having a flow path having a portion that is linear and a portion that is partially circumferential. In some embodiments, the portion of the flow path that is linear and the portion of the flow path that is partially circumferential lie in the same plane. In other embodiments, the portion of the flow path that is linear extends along an axis that is tangential to, or substantially tangential to, the portion of the flow path that is partially circumferential. In other embodiments, the portion of the flow path that is partially circumferential is partially spherical, or substantially spherical. In these embodiments, the portion of the flow path that is linear can extend along an axis that is tangential to, or substantially tangential to, the hypothetical sphere of which the partially circumferential portion is a portion.

An example device for extracorporeal conditioning of blood comprises a housing and a conditioning module having a fluid inlet having a flow path that is partially linear and partially circumferential and a fluid outlet having a flow path that is partially linear and partially circumferential, and including a plurality of fiber mats and potting material that defines a circumferential border on the plurality of fiber mats to form a substantially circular flow path through the plurality of fiber mats.

Another example device for extracorporeal conditioning of blood comprises a housing and a conditioning module having a fluid inlet having a flow path that is partially linear and partially circumferential and a fluid outlet having a flow path that is partially linear and partially circumferential, and including a plurality of fiber mats and potting material that defines a circumferential border on the plurality of fiber mats to form a substantially cylindrical internal chamber providing a substantially circular cross-sectional flow path through the plurality of fiber mats.

Another example device for extracorporeal conditioning of blood comprises a housing and a conditioning module having a fluid inlet and a fluid outlet, and including a plurality of fiber mats and potting material that defines a circumferential border on the plurality of fiber mats to form a substantially cylindrical internal chamber providing a substantially circular cross-sectional flow path through the plurality of fiber mats. The fluid inlet extends along a first axis that is substantially perpendicular to a plane containing the plurality of fiber mats. The fluid outlet extends along a second axis that is substantially perpendicular to the plane containing the plurality of fiber mats. A first end of the fluid inlet has a first internal height perpendicular to the first axis and a second end of the fluid inlet has a second internal height perpendicular to the first axis. The second internal height is less than the first internal height. The fluid inlet includes a sloped internal surface that devices a curvilinear surface that transitions the inner lumen of the fluid inlet from the first internal height to the second internal height.

Another example device for extracorporeal conditioning of blood comprises a housing and a conditioning module having a fluid inlet and a fluid outlet, and including a first fiber assembly and a second fiber assembly. A potting material defines a circumferential border on the first fiber assembly and the second fiber assembly to form a substantially cylindrical internal module chamber providing a substantially circular cross-sectional flow path through the first fiber assembly and the second fiber assembly within the conditioning module. A separating member separates the first fiber assembly from the second fiber assembly within the potting material and outside of the circumferential border relative to the internal module chamber. Within the internal module chamber, a terminal mat of the first fiber assembly is in direct contact with an adjacent terminal mat of the second fiber assembly along the entire interface of these terminal mats and fiber assemblies within the internal module chamber.

Another example device for extracorporeal conditioning of blood comprises a housing defining a housing chamber; a conditioning module disposed within the housing chamber, the conditioning module comprising an external frame, an inlet cover, an outlet cover, and defining an internal chamber; a first fiber assembly disposed within the internal chamber and having a first peripheral edge; a second fiber assembly disposed within the internal chamber and having a second peripheral edge, the second fiber bundle disposed adjacent and in direct contact with the first fiber bundle; potting material disposed throughout the first and second peripheral edges to create a circumferential seal that defines a passageway through the first and second fiber assemblies that has a substantially circular cross-sectional shape; a separating member disposed on the external frame and extending into the potting material, the separating member separating the first peripheral edge from the second peripheral edge; and a fluid inlet disposed on the inlet cover and extending along a first axis that is substantially perpendicular to the first fiber assembly, the fluid inlet having an inlet lumen, a first inlet end and, a second inlet end positioned between the first inlet end and the first fiber assembly, and an internal curvilinear surface, the inlet lumen in fluid communication with the passageway and having a first internal inlet height perpendicular to the first axis at the first inlet end and a second internal inlet height perpendicular to the first axis at the second inlet end, the fluid inlet having a first inlet end and a second inlet end positioned between the first inlet end and the first fiber assembly, the inlet lumen having a first internal inlet height perpendicular to the first axis at the first inlet end and a second internal inlet height perpendicular to the first axis at the second inlet end, the second internal inlet height being less than the first internal inlet height; and a fluid outlet disposed on the outlet cover and extending along a second axis that is substantially perpendicular to the first fiber assembly, the fluid outlet having an outlet lumen in fluid communication with the passageway.

Various example methods of manufacturing a potted fiber assembly are described.

An example method of manufacturing a potted fiber assembly comprises assembling a first fiber assembly comprising a first plurality of fiber mats and a second plurality of fiber mats such that fibers of the first plurality of fiber mats are arranged substantially orthogonally to the fibers of the fiber mats of the second plurality of fiber mats; cutting the first fiber assembly to form fiber assembly precursor having a substantially square shape; placing the fiber assembly precursor into a cartridge adapted to be attached to a centrifuge to spin the fiber assembly precursor on its central axis; placing potting material into the cartridge; spinning the cartridge and fiber assembly precursor in the centrifuge to achieve a radial dispersion of the potting material throughout the fiber assembly precursor to form a fiber assembly in which the potting material forms a circumferential border and defines a flow path having a substantially circular cross-sectional shape.

Various example methods of manufacturing a device for extracorporeal conditioning of blood are described.

An example method of manufacturing a device for extracorporeal conditioning of blood comprises assembling a first fiber assembly comprising a first plurality of fiber mats and a second plurality of fiber mats such that fibers of the first plurality of fiber mats are arranged substantially orthogonally to the fibers of the fiber mats of the second plurality of fiber mats; cutting the first fiber assembly to form a fiber assembly precursor having a substantially square shape; placing the fiber assembly precursor into a cartridge adapted to be attached to a centrifuge to spin the fiber assembly precursor on its central axis; placing potting material into the cartridge; spinning the cartridge and fiber assembly precursor in the centrifuge to achieve a radial dispersion of the potting material throughout the fiber assembly precursor to form a fiber assembly in which the potting material forms a circumferential border on the fiber assembly that defines a substantially cylindrical internal chamber providing a substantially circular cross-sectional flow path through the fiber mats of the fiber assembly; placing the fiber assembly into a conditioning module; placing the conditioning module into the interior chamber cooperatively defined by first and second housing elements to form a device for extracorporeal conditioning of blood.

Additional understanding of the claimed devices and methods can be obtained by reviewing the detailed description of selected examples, below, with reference to the appended drawings.

DETAILED DESCRIPTION OF SELECTED EXAMPLES

The following detailed description and the appended drawings describe and illustrate various example devices and methods. The description and illustration of these examples enable one skilled in the art to make and use examples of the inventive devices and to perform examples of the inventive methods. They do not limit the scope of the claims in any manner.

As used herein, the term "substantially circular cross-sectional shape," and grammatically related terms, refers to a cross-sectional shape that is either perfectly circular or immediately recognizeable as circular despite not being perfectly circular. A cross-sectional shape that is not perfectly circular due to acceptable tolerances suitable for the manufacturing of the types of devices described herein but that is immediately recognizeable as circular is considered to be substantially circular.

As used herein, the term "substantially orthogonally," and grammatically related terms, refers to a relative structural arrangement of two items in which one item is either perfectly positioned orthogonal to the other item or in which one item is positioned in a manner that is immediately recognizeable as orthogonal to the other item despite not being perfectly orthogonal to the other item. A relative structural arrangement between two items that is not perfectly orthogonal due to acceptable tolerances suitable for the manufacturing of the types of devices described herein but that is immediately recognizeable as orthogonal is considered to be substantially orthogonally positioned.

As used herein, the term "substantially parallel," and grammatically related terms, refers to a relative structural arrangement of two items in which one item is either perfectly positioned parallel to the other item or in which one item is positioned in a manner that is immediately recognizeable as parallel to the other item despite not being perfectly parallel to the other item. A relative structural arrangement between two items that is not perfectly parallel due to acceptable tolerances suitable for the manufacturing of the types of devices described herein but that is immediately recognizeable as parallel is considered to be substantially parallel.

As used herein, the term "substantially perpendicular," and grammatically related terms, refers to a relative structural arrangement of two items in which one item is either perfectly positioned perpendicular to the other item or in which one item is positioned in a manner that is immediately recognizeable as perpendicular to the other item despite not being perfectly perpendicular to the other item. A relative structural arrangement between two items that is not perfectly perpendicular due to acceptable tolerances suitable for the manufacturing of the types of devices described herein but that is immediately recongnizeable as perpendicular is considered to be substantially perpendicular.

Figure 1:
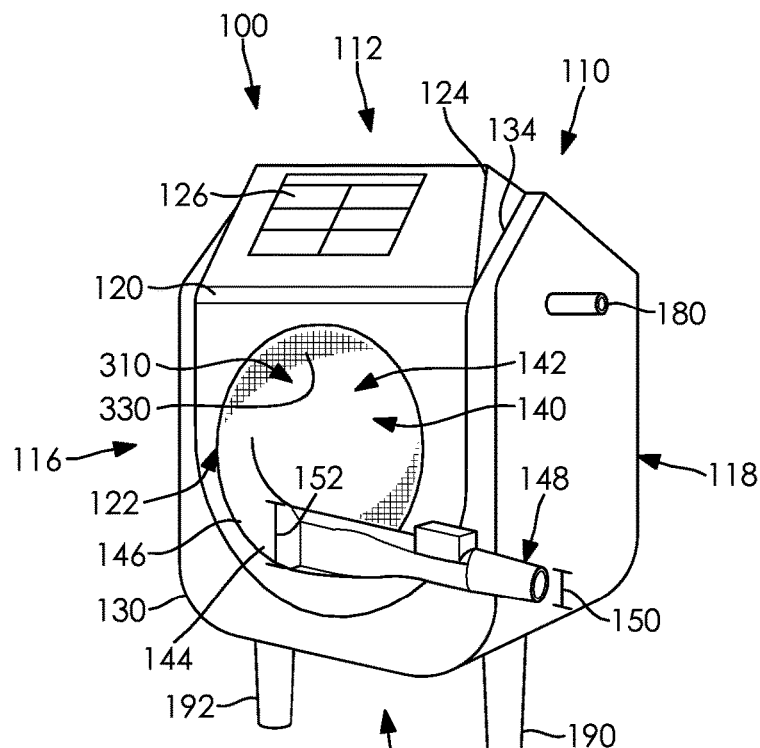
FIG. 1 is a perspective view of a first example device for extracorporeal conditioning of blood.
Figure 2:
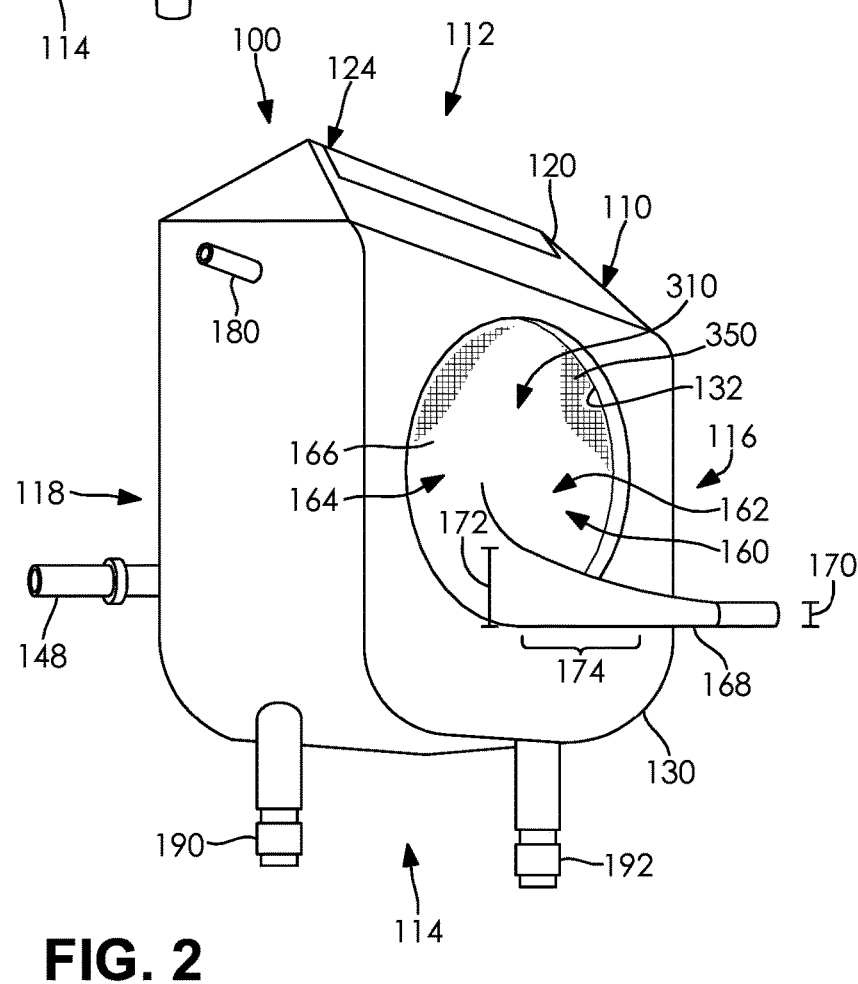
FIG. 2 is another perspective view of the first example device.
Figure 3:
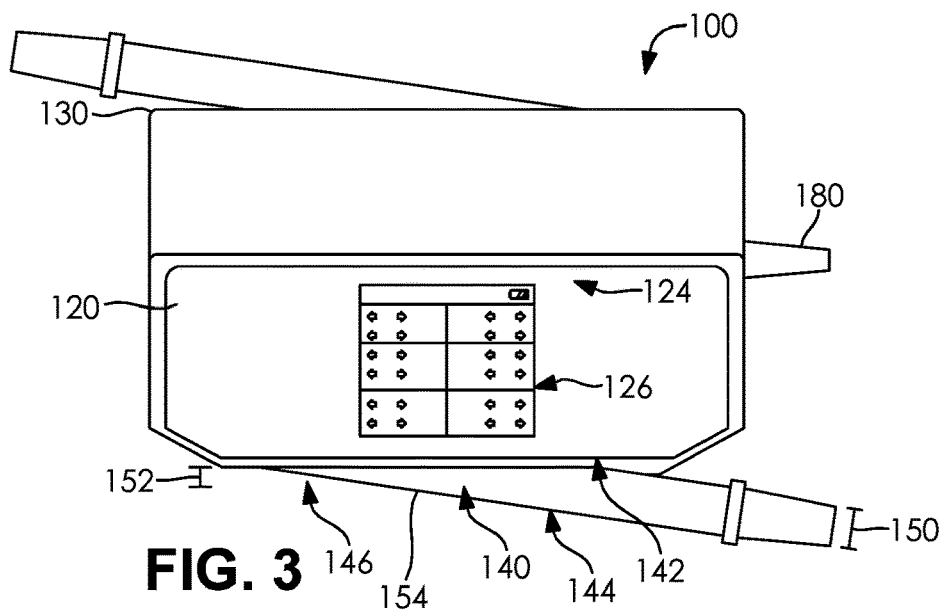
FIG. 3 is a top view of the first example device.
Figure 3A:
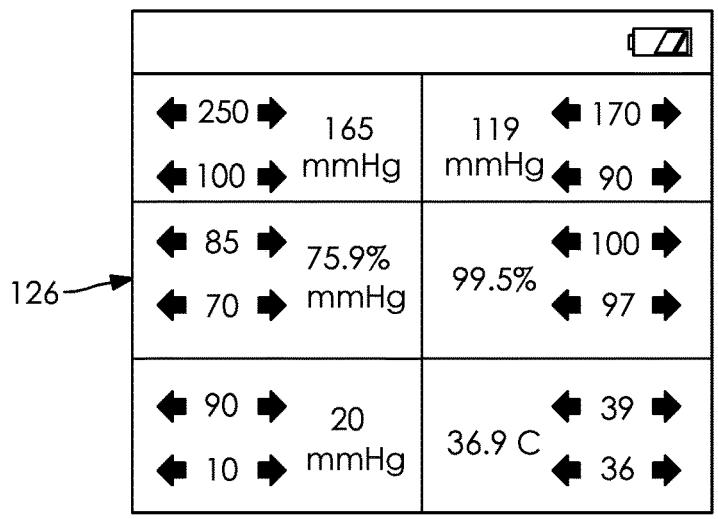
FIG. 3A is an isolated magnified view of the information panel of the first example device.

Each of FIGS. 1, 2, 3, 3A, 4, 5, 6, 7, 8, 9, 9A, 9B, 9C, 9D, and 10 illustrates an example device 100 for extracorporeal conditioning of blood, or an assembly or component of the example device 100. Each of FIGS. 1, 2, and 3 illustrates the device 100 in a fully assembled form; each of FIGS. 3A, 4, 5, 6, 7, 8, 9, 9A, 9B, 9C, 9D, and 10 illustrates an assembly or component of the device 100 isolated, to a degree, from other components and/or portions of the device 100.

The device 100 has a housing 110 that provides, generally, a first end 112, a second end 114, a first side 116, and a second side 118. The first end 112 is generally opposite the second end 114, and the first side 116 is generally opposite the second side 118. The housing 110 has a first housing element 120 and a second housing element 130 that are attached to each other to form the housing 110. It is noted that, while the illustrated embodiment includes first 120 and second 130 housing elements, a single unitary housing element could also be used in an embodiment.

The first housing element 120 defines an opening 122 and a control chamber 124. An information panel 126 is secured to the first housing element 120 and is disposed adjacent the control chamber 124. The second housing element 130 defines an opening 132. The first 120 and second 130 housing elements cooperatively define an interior chamber 134.

An inlet cover 140 is disposed in the opening 122 of the first housing element 120. As best illustrated in FIG. 1, the inlet cover 140 spans across the opening 122 of the first housing element 120. The inlet cover 140 defines a window 142 that allows visual observation of fluid flowing through the inlet cover 140 within the interior chamber 134 of the device 100. Also, the inlet cover 140 defines structure that provides fluid access to the components disposed within the interior chamber 134 of the device 100, such as conditioning module 310 as described in detail below. As best illustrated in FIG. 1, the inlet cover 140 defines an integrally formed inlet 144 that provides fluid communication between the internal chamber defined by the conditioning module 310 and the environment external to the device 100, which can include an attached fluid supply line, such as in an extracorporeal blood circulation circuit. A seal can be included along the perimeter of the opening 122 where the inlet cover 140 interfaces with the first housing element 120.

In the illustrated embodiment, the inlet 144 has a flow path that is linear at one end and partially circumferential at the other end. Thus, the port 148 defines a linear flow path that gradually transitions to a partial circumferential flow path 146 in the portion of the inlet 144 that is disposed within the interior chamber 134 of the device 100 and immediately adjacent the conditioning module 310 of the device 100. The port 148 provides a generally round opening at one end and a partial-circumferential opening opens to the internal chamber defined by conditioning module 310 within the interior chamber 134 at the other end to provide fluid access to the first 330 and second 350 fiber assemblies disposed within the conditioning module 310. The inlet 144 has a first internal height 150 at the port 148 and, at the other end, a second internal height 152. Each of the first 150 and second 152 internal heights are measured along a transverse axis of the inlet 144 that is disposed orthogonally to the lengthwise axis of the inlet 144. In the illustrated embodiment, the first height 150 is less than the second height 152. As a result, the inlet 144 defines a taper 154 that transitions from a first height 150 at the port 148 to a second, greater height 152 at the other end where the inlet 144 interfaces with the conditioning module 310. This structural arrangement is considered advantageous at least because it facilitates distribution of blood across the cross-sectional circular flow path defined by the conditioning module 310. Other arrangements of first and second heights can be used in a device according to a particular embodiment. For example, the inlet of a device according to an embodiment can have a first height that is greater than, equal to, or substantially equal to the second height. These alternative arrangements may not provide the advantages, though, that the inventors have identified for the illustrated example.

An outlet cover 160 is disposed in the opening 132 of the second housing element 130. As best illustrated in FIG. 2, the outlet cover 160 spans across the opening 132 of the second housing element 130. The outlet cover 160 defines a window 162 that allows visual observation of fluid flowing out of the components disposed within the interior chamber 134 of the device 100, such as the conditioning module 310, and through the outlet cover 160. Also, the outlet cover 160 defines structure that provides fluid egress from components disposed within the interior chamber 134 of the device 100, such as conditioning module 310 as described in detail below. As best illustrated in FIG. 2, the outlet cover 160 defines an integrally formed outlet 164 that provides fluid communication between the internal chamber defined by conditioning module 310 of the device 100 and the environment external to the device 100, which can include an attached fluid supply line, such as in an extracorporeal blood circulation circuit. A seal can be included along the perimeter of the opening 132 where the outlet cover 160 interfaces with the second housing element 130.

In the illustrated embodiment, the outlet 164 has a flow path that is linear at one end and partially circumferential at the other end. Thus, the port 168 defines a linear flow path that gradually transitions to a partial circumferential flow path 166 in the portion of the outlet 164 that is disposed within the interior chamber 134 of the device 100 and immediately adjacent the conditioning module 310 of the device 100. The port 168 provides a generally round opening at one end and a partial-circumferential opening opens to the internal chamber defined by conditioning module 310 within the interior chamber 134 at the other end to provide fluid egress from the first 330 and second 250 fiber assemblies disposed within the conditioning module 310. The outlet 164 has a first internal height 170 at the port 168 and, at the other end, a second internal height 172. Each of the first 170 and second 172 internal heights are measured along a transverse axis of the outlet 164 that is disposed orthogonally to the lengthwise axis of the outlet 164. In the illustrated embodiment, the first height 170 is less than the second height 172. As a result, the outlet 164 defines a taper 174 that transitions from a first height 170 at the port 168 to a second, greater height 172 at the other end where the outlet 164 interfaces with the conditioning module 310. This structural arrangement is considered advantageous at least because it facilitates collection of exiting blood from across the cross-sectional circular flow path defined by the conditioning module 310. Other arrangements of first and second heights can be used in a device according to a particular embodiment. For example, the outlet of a device according to an embodiment can have a first height that is greater than, equal to, or substantially equal to the second height. These alternative arrangements may not provide the advantages, though, that the inventors have identified for the illustrated example.

Generally, as best illustrated in FIG. 2, the port 148 of the inlet 144 extends away from the housing 110 in a first direction and the port 168 of the outlet 164 extends away from the housing 110 in a second, opposite direction. As a result, the partial circumferential path 146 defined by the inlet 144 extends in a first circumferential direction and the partial circumferential path 166 defined by the outlet 164 extends in a second circumferential direction that is the substantial opposite of the first circumferential direction.

Figure 9:
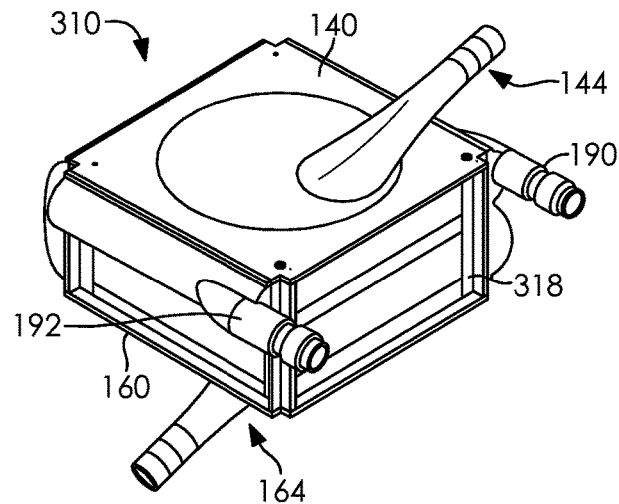
FIG. 9 is a perspective view of the conditioning module of the first example device.
Figure 9A:
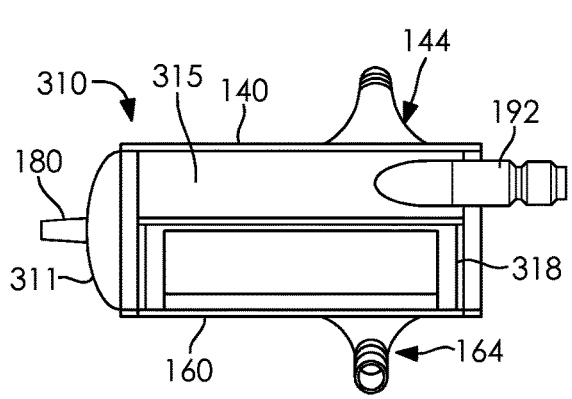
FIG. 9A is a side view of the conditioning module of the first example device.
Figure 9B:
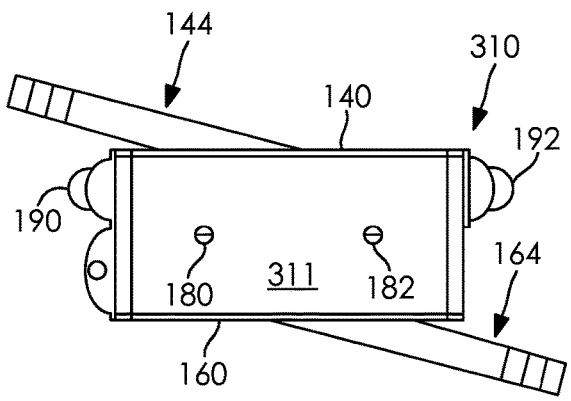
FIG. 9B is another side view of the conditioning module of the first example device.
Figure 9C:
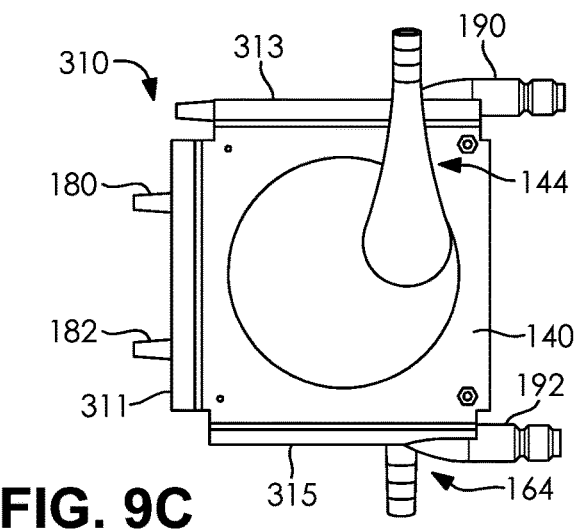
FIG. 9C is a top view of the conditioning module of the first example device.
Figure 9D:
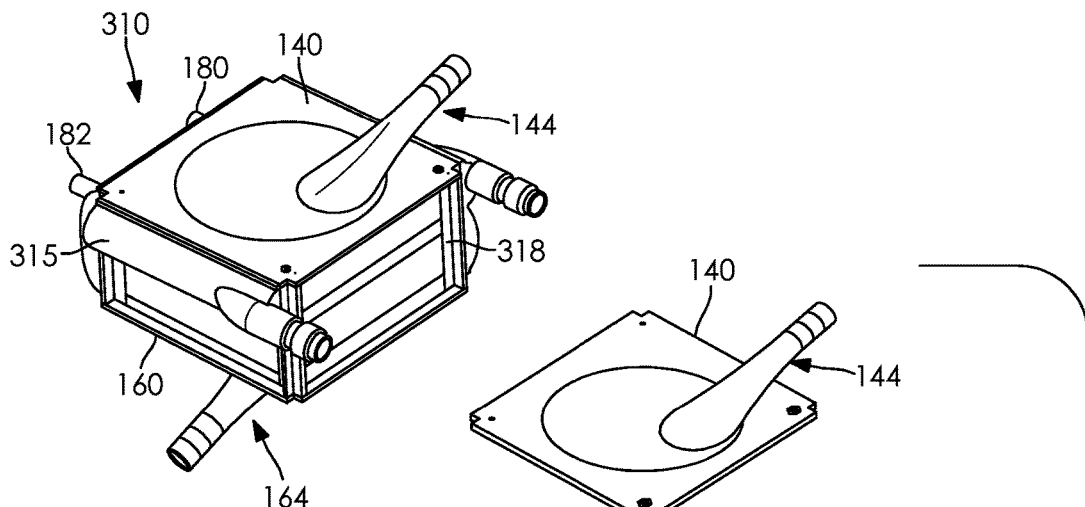
FIG. 9D is another perspective view of the conditioning module of the first example device.
Figure 10:
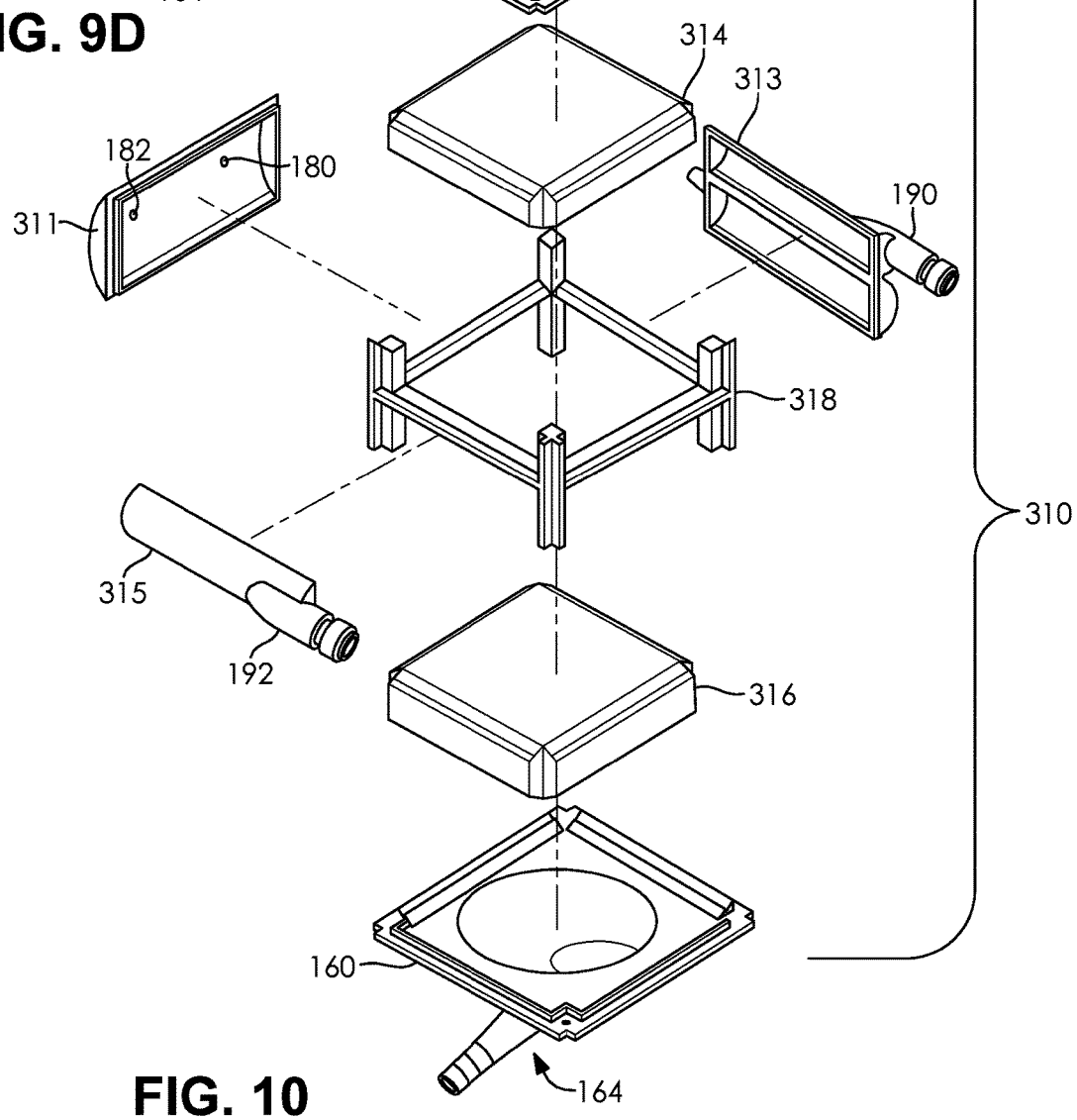
FIG. 10 is an exploded view of the conditioning module of the first example device.

In the illustrated embodiment, as best illustrated in FIGS. 9 and 10, and described in detail below, the inlet cover 140 and the outlet cover 160 are components of a conditioning module 310 that is disposed within the interior chamber 134 of the device 100.

The second housing element 130 defines openings that receive a gas inlet 180 and a gas outlet 182 of a conditioning module 310. As described in more detail below, the gas inlet 180 and gas outlet 182 cooperate with a fiber assembly to define a gas pathway 184 that enables a delivered gas, such as oxygen or other suitable gas, to flow through the device 100 and interface with fluid, such as blood, flowing through the device to achieve a desired conditioning, such as gas exchange and oxygenation, of the fluid. The second housing element 130 also defines openings that receive a heat exchange fluid inlet 190 and a heat exchange fluid outlet 192 of a conditioning module 310. As described in more detail below, the heat exchange fluid inlet 190 and heat exchange fluid outlet 192 cooperate with a fiber assembly to define a heat exchange fluid pathway 194 that enables a delivered heat exchange fluid, such as sterile water or other suitable heat exchange fluid, to flow through the device 100 and interface with fluid, such as blood, flowing through the device to achieve a desired conditioning, such as warming and/or heating, of the fluid.

Figure 4:
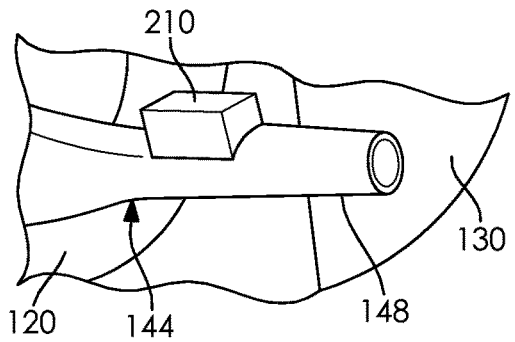
FIG. 4 is an isolated magnified view of the inlet of the first example device.
Figure 5:
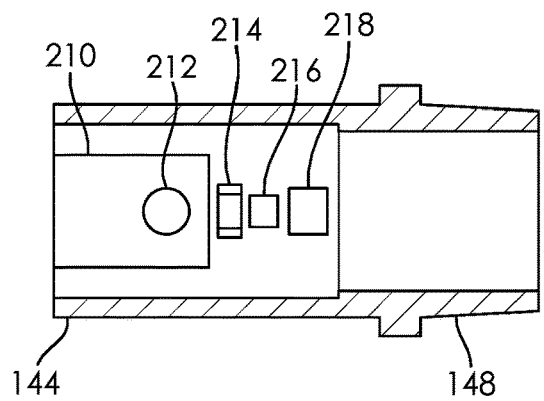
FIG. 5 is a bottom, isolated magnified view of the inlet and sensor module of the first example device.

As best illustrated in FIGS. 1 and 4, a sensor module 210 is disposed on the inlet 144. As best illustrated in FIG. 5, which illustrates the underside of the sensor module 210 as viewed through the inlet 144, the sensor module 210 in the illustrated embodiment includes a first sensor 212, a second sensor 214, a third sensor 216, and a fourth sensor 218. Each of the sensors 212, 214, 216, 218 is positioned on the surface of the inlet 144 such that the sensor can perform appropriate measurements and/or calculations on fluid flowing through the inlet 144. Any suitable sensors can be included in a sensor module in a device according to a particular embodiment, and a skilled artisan will be able to select suitable sensors for a particular device based on various considerations, including the nature of the fluid for which the device is intended to be used, characteristics of a particular patient and/or treatment regimen, and other considerations. Examples of suitable sensors include, but are not limited to, pressure sensors, temperature sensors, chemical sensors, gas sensors, optical sensors, infrared sensors, and other sensors. The sensor module 210 is operably connected to a controller within the control chamber 124, such as by an electrical, wireless, or other operable connection suitable for transmitting sensor data and/or other information to a controller adapted to process and/or display information relating to the sensor data and/or other information to a user of the device 100. For example, the sensor module 210 in the illustrated embodiment is connected a controller disposed within the control chamber 124 by a ribbon cable. The controller processes information relating to sensor data and/or other information transmitted to the controller from the sensor module 210 and displays information relating to the sensor data and/or other information on the information panel 126, which can be readily viewed and accessed by a user.

A sensor module can be disposed on the outlet 164 as well, if desired. If included, a sensor module disposed on the outlet 164 can be the same as the sensor module 210 disposed on the inlet 144, or can be different from the sensor module 210 disposed on the inlet 144. Also, it is noted, that an embodiment can have a sensor module disposed on the outlet 164 and not on the inlet 144. One or more sensor modules can be disposed in other suitable locations within the device in lieu of or in addition to the sensor module(s) disposed on the inlet and/or outlet. For example, one or more sensor modules can be disposed within the conditioning module of a device according to a particular embodiment.

The conditioning module 310 is disposed within the interior chamber 134 of the device 100. The conditioning module 310 provides the structure that enables fluid flowing through the device to interface with gas flowing through the gas pathway 194 and with heat exchange fluid flowing through the heat exchange pathway 196 to achieve the desired conditioning of the fluid.

Figure 6:
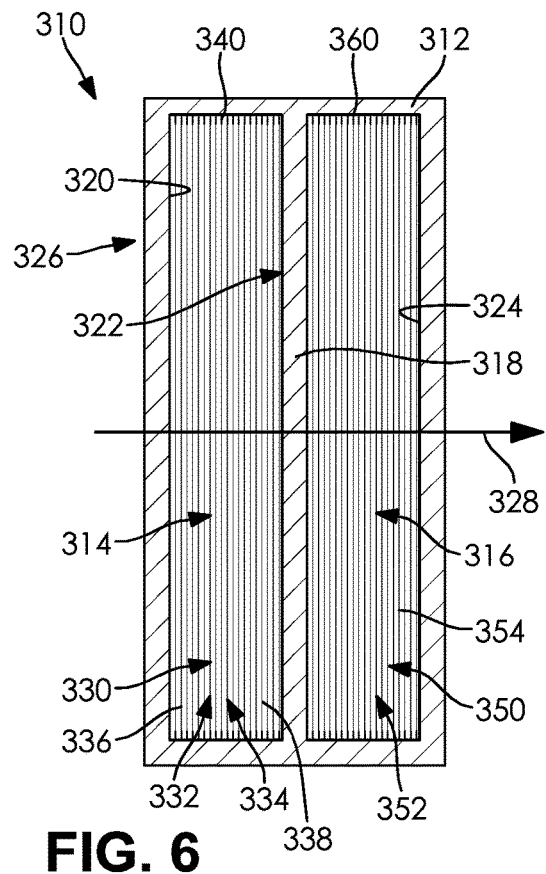
FIG. 6 is a side view of the exchange and heating assembly of the first example device.

As best illustrated in FIGS. 6 and 10, the conditioning module 310 has a first chamber 314 and a second chamber 316. A frame 318 is disposed between the first 314 and second 316 chambers and substantially fixes the relative positions of the chambers 314, 316. Wall members 311, 313, 315 are attached to the frame 318 and define various inlets, outlets, and passages to direct fluid flow through portions of the conditioning module 310. For example, wall member 311 defines gas inlet 180 and gas outlet 182, wall member 313 defines heat exchange fluid inlet 190, and wall member 315 defines heat exchange fluid outlet 192. In the illustrated embodiment, the frame 318 is a separate component that is assembled with the first 314 and second 316 chambers. It is noted, though, that frame could be integrally formed with the first 314 and second 316 chambers in an embodiment. If a separate frame is used, such as frame 318, the frame is advantageously attached to the first 314 and second 316 chambers, such as with application of an appropriate sealant, formation of an a suitable joint, such as a weld joint, or through other suitable means for attaching members to each other. The inlet cover 140 is secured to the frame 318 and disposed adjacent the first chamber 314. The outlet cover 160 is secured to the frame 318 and disposed adjacent the second chamber 316.

As described in more detail below, the conditioning module 310 defines a passageway 326 that extends from the circumferential recess of the inlet cover 140, through the first chamber 314 and the second chamber 316 and to the circumferential recess of the outlet cover 160. On the inlet side, the passageway 326 is in fluid communication with the inlet 144 of the inlet cover 140 and the outlet 164 of the outlet cover 160. Thus, the passageway 326 extends through the conditioning module 310, allowing fluid to flow through the first 314 and second 316 chambers of the conditioning module 310 and, indeed, from the inlet 144 to the outlet 164. Also, as described in more detail below, the passageway 326 has a substantially circular cross-sectional shape with dimensions substantially similar to the circumferential recesses defined by the inlet cover 140 and the outlet cover 160. In use, fluid flows through the passageway 326, and through the first 314 and second 316 chambers of the conditioning module 310, in the direction of arrow 328.

Figure 7:
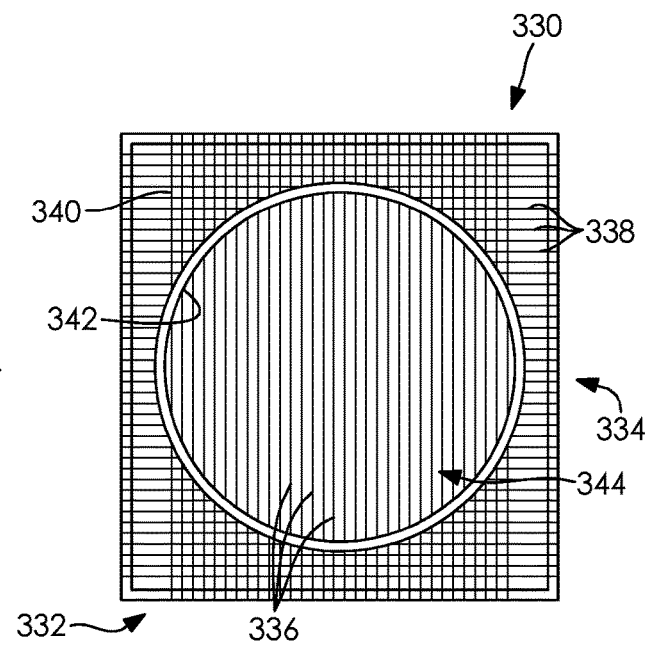
FIG. 7 is a front view of a fiber assembly of the first example device.
Figure 8:
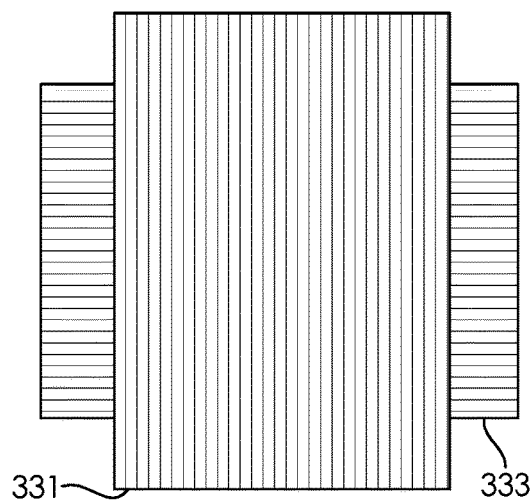
FIG. 8 is a front view of two fiber mats prior to inclusion in a fiber assembly.

A first fiber assembly 330 is disposed within the first chamber 314. Similarly, a second fiber assembly 350 is disposed within the second chamber 316. The first fiber assembly 330 includes a first plurality of fiber mats 332 and a second plurality of fiber mats 334. Each fiber mat of the first plurality of fiber mats 332 includes a plurality of hollow fibers 336. Similarly, each fiber mat of the second plurality of fiber mats 334 includes a plurality of hollow fibers 338. As best illustrated in FIGS. 7 and 8, the first fiber assembly 330 includes fiber mats of the first plurality of fiber mats 332 arranged such that its fibers 336 are arranged substantially orthogonally to the fibers 338 of the fiber mats of the second plurality of fiber mats 334. Also, as best illustrated in FIG. 7, a potting material 340 is disposed throughout the first fiber assembly 330 to create a circumferential seal 342 that defines a flow path through the first fiber assembly 330 that has a substantially circular cross-sectional shape 344 with dimensions substantially similar to the circumferential recess defined by the inlet cover 140.

The second fiber assembly 350 includes a third plurality of fiber mats 352. Each fiber mat of the third plurality of fiber mats 352 includes a plurality of hollow fibers 354. The second fiber assembly 350 includes fiber mats of the third plurality of fiber mats 352 arranged such that its fibers 354 are arranged substantially parallel to the fibers 336 of the first plurality of fiber mats 332 and orthogonally to the fibers 338 of the fiber mats of the second plurality of fiber mats 334. A potting material 360 is disposed throughout the second fiber assembly 350 to create a circumferential seal 362 that defines a flow path through the second fiber assembly 350 that has a substantially circular cross-sectional shape 364 with dimensions substantially similar to the circumferential recess defined by the outlet cover 160. The second fiber assembly 350 can include a fourth plurality of fiber mats that is interspersed with the third plurality of fiber mats 352 and arranged such that its fibers are arranged substantially parallel to the fibers 338 of the second plurality of fiber mats 334 and orthogonally to the fibers 336 of the fiber mats of the first plurality of fiber mats 332 and of the third plurality of fiber mats 352.

FIG. 8 illustrates a fiber mat 331 of the first plurality of fiber mats 332 arranged adjacent to a fiber mat 333 of the second plurality of fiber mats 334 such that its fibers 336 are arranged substantially orthogonally to the fibers 338 of the fiber mats of the second plurality of fiber mats 334. A series of fiber mats of the first 332 and second 334 pluralities of fiber mats can be arranged in this manner and interspersed with each other to assemble a precursor to the first fiber mat assembly 330. Once a desired number of fiber mats of the first 332 and second 334 pluralities of fiber mats are arranged in this manner and interspersed with each other, the precursor assembly can be cut to form a square. Potting material can then be added, such as using a method described below, to create the first fiber assembly 330. The mats are cut after potting material is added to expose open ends of the fibers.

The fiber assemblies in a device according to an embodiment can be constructed and arranged in any suitable manner and a skilled artisan will be able to select a suitable construction for a device according to a particular embodiment based on various considerations, such as the types of fluids that will be passed through the hollow fibers of the fiber mats in the fiber assemblies. For example, in the illustrated embodiment, the first fiber assembly 330 and the second fiber assembly 350 include approximately the same number of fiber mats. Each of the fiber assemblies 330, 350 can be used with one or two fluids, because of the orthogonal arrangements of the respective pluralities of fiber mats. For example, the first fiber assembly 330 can be used to pass a gas exchange fluid through the first plurality of fiber mats 332 and a heat exchange fluid through the second plurality of fiber mats 334. Also, the second fiber assembly 350 can be used to pass a gas exchange fluid through the third plurality of fiber mats 352 and, if included, also through the fourth plurality of fiber mats. Alternatively, the second fiber assembly 350 can be used in the same manner as the first fiber assembly 330. Thus, the second fiber assembly can be used to pass a gas exchange fluid through the third plurality of fiber mats 352 and to pass a heat exchange fluid through the fourth plurality of fiber mats.

Figure 11:
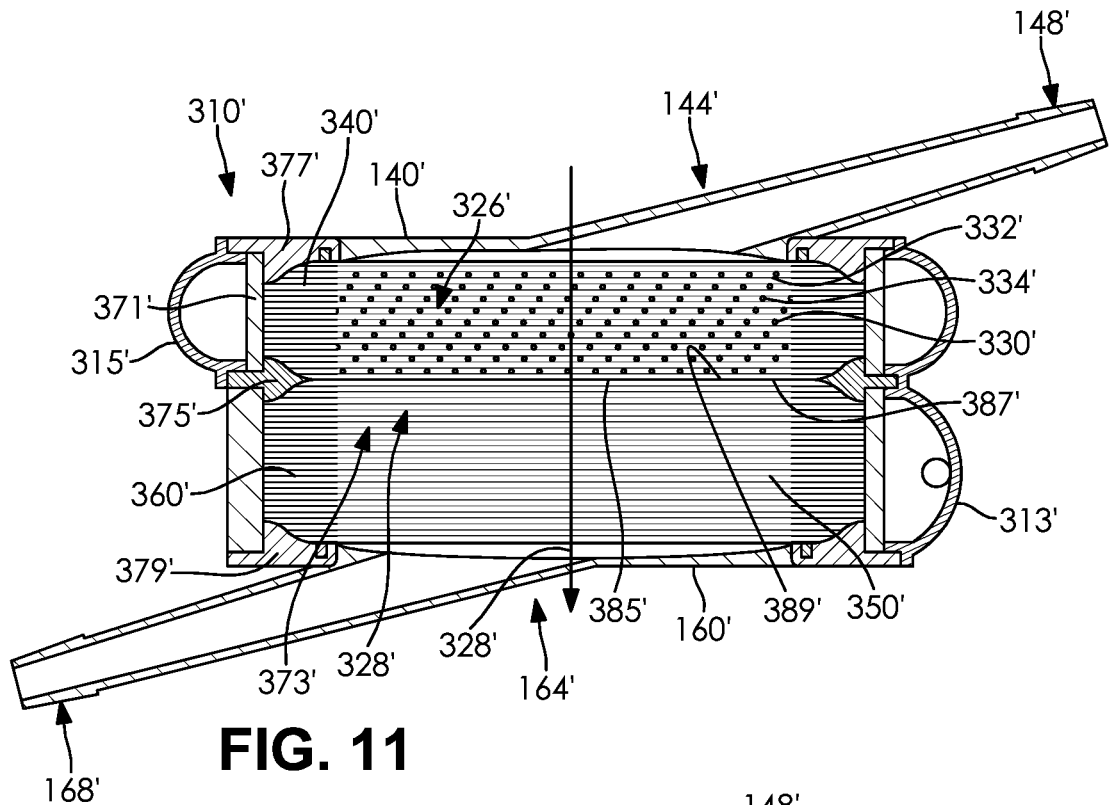
FIG. 11 is a sectional view of an alternative conditioning module.
Figure 12:
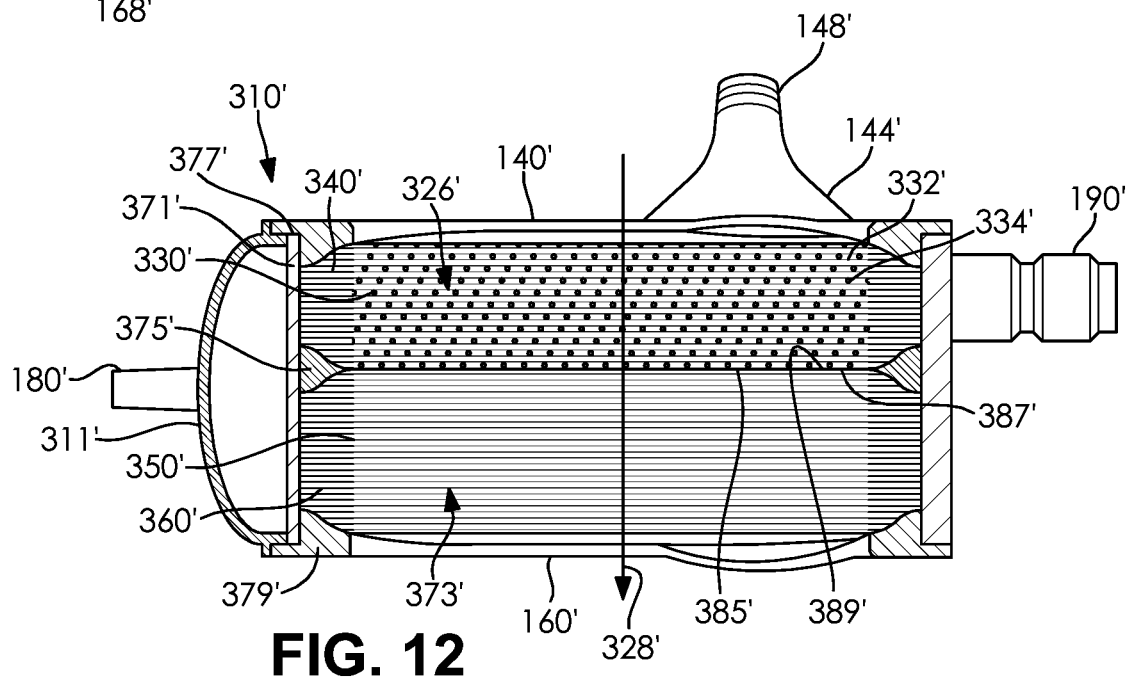
FIG. 12 is another sectional view of the alternative conditioning module illustrated in FIG. 11.

FIGS. 11 and 12 illustrate an alternative conditioning module 310'. The alternative conditioning module 310' can be used with the first example device 100, in lieu of the conditioning module 310 described above. Conditioning module 310' is similar to conditioning module 310 described above, except as detailed below. Thus, conditioning module 310' is disposed within the interior chamber of a device, such as device 100. The conditioning module 310' provides the structure that enables fluid flowing through the device to interface with gas flowing through a gas pathway and with heat exchange fluid flowing through a heat exchange pathway to achieve a desired conditioning of the fluid.

The conditioning module 310' has an external frame 371' to which the inlet cover 140' is secured. The outlet cover 160' is also secured to the external frame 371' and positioned opposite the inlet cover 140'. The external frame 371', inlet cover 340', and outlet cover 160' cooperatively define an internal module chamber 373'. The conditioning module 310' defines a passageway 326' that extends from the circumferential recess of the inlet cover 140', through the internal module chamber 373' and to the circumferential recess of the outlet cover 160'. On the inlet side, the passageway 326' is in fluid communication with the inlet 144' of the inlet cover 140'; on the outlet side, the passageway 326' is in fluid communication with the outlet 164' of the outlet cover 160'. Thus, the passageway 326' extends through the conditioning module 310', allowing fluid to flow through the internal module chamber 373' of the conditioning module 310' and, indeed, from the inlet 144' to the outlet 164'. Also, the passageway 326' is bounded by potting material 340' and 360', which has a circumferential border within the internal module chamber 373' to give the passageway 326' a substantially circular cross-sectional shape with dimensions substantially similar to the circumferential recesses defined by the inlet cover 140' and the outlet cover 160'. In use, fluid flows through the passageway 326', and through the internal module chamber 373' of the conditioning module 310', in the direction of arrow 328'.

A first fiber assembly 330' is disposed within the internal module chamber 373'. Similarly, a second fiber assembly 350' is disposed within the internal module chamber 373'. The first fiber assembly 330' includes first 332' and second 334' pluralities of fiber mats arranged such that the fibers of the first plurality of mats 332' are arranged substantially orthogonally to the fibers of the fiber mats of the second plurality of fiber mats 334'. Potting material 340' is disposed throughout the first fiber assembly 330' to create a circumferential seal that defines a flow path through the first fiber assembly 330' that has a substantially circular cross-sectional shape with dimensions substantially similar to the circumferential recess defined by the inlet cover 140. The flow path defined by the potting material 340' comprises a portion of the passageway 326'.

The second fiber assembly 350' includes third 352' and fourth 354' pluralities of fiber mats arranged such that the fibers of the third plurality of mats 352' are arranged substantially orthogonally to the fibers of the fiber mats of the fourth plurality of fiber mats 354'. Potting material 360' is disposed throughout the second fiber assembly 350' to create a circumferential seal that defines a flow path through the second fiber assembly 350' that has a substantially circular cross-sectional shape with dimensions substantially similar to the circumferential recess defined by the outlet cover 160'. The flow path defined by the potting material 360' comprises a portion of the passageway 326'.

In this example, the conditioning module 310' lacks an internal frame member that separates the first 330' and second 350' fiber assemblies. In this example, as illustrated in FIGS. 11 and 12, the first 330' and second 350' fiber assemblies are in direct contact with each other. Indeed, a terminal mat 387' of the first fiber assembly 330' is in direct contact with an adjacent terminal mat 389' of the second fiber assembly 350' along the entire interface 385' between the first 330' and second 350 fiber assemblies within the passageway 326'. There is no other structure disposed between the first 330' and second 350' fiber assemblies within the passageway 326' bounded by potting 340', 360'.

External frame 371' includes separating member 375' that extends into the internal module chamber 373'. The separating member 375' extends along one or more internal surfaces of the external frame 371' and can extend entirely around the internal module chamber 373' to provide a circumferential separating member. The separating member 375' extends into and partially separates potting 340' and potting 360', forcing the peripheral edges of the innermost fiber mats of the first fiber assembly 330' toward the inlet cover 140' and peripheral edges of the innermost fiber mats of the second fiber assembly toward the outlet cover 160'. External frame 371' also defines an inlet projection 377' and an outlet projection 379', each of which extends inwardly into the internal module chamber 373'. The inlet projection 377' forces the peripheral edges of the fiber mats of the first fiber assembly 330' that are relatively close to the inlet cover 140' away from the underside of the inlet cover 140'. Similarly, the outlet projection 379' forces the peripheral edges of the fiber mats of the second fiber assembly 350' that are relatively close to the outlet cover 160' away from the underside of the outlet cover 160'. Similar to the separating member 375', each of the inlet projection 377' and the outlet projection 379' extends along one or more internal surfaces of the external frame 371' and can extend entirely around the internal module chamber 373' to provide a circumferential projection if desired. Each of the separating member 375', inlet projection 377', and outlet projection 379' can comprise a separate member attached to the external frame 371', or can be integrally formed by the external frame 371'. Furthermore, the inlet projection can be a separate member attached to the inlet cover or can be integrally formed by the inlet cover. Similarly, the outlet projection can be a separate member attached to the outlet cover or can be integrally formed by the outlet cover.

The separating member 375', inlet projection 377', and outlet projection 379' cooperate to partially separate the peripheral edge of the first fiber assembly 330' from the peripheral edge of the second fiber assembly 350' and to taper the peripheral edges of the fiber mats of the first 330' and second 350' fiber assemblies to a shortened height within the width of the respective potting 340', 360'. This structural configuration is considered advantageous at least because it allows for direct contact between the first 330' and second 350' fiber assemblies, as described above, while still maintaining a peripheral separation of the assemblies 330', 350'. Furthermore, it provides beneficial contact between the first 330' and second 350' fiber assemblies within the internal module chamber 373' by reducing the potential for gaps to form between the fiber mats of the assemblies 330', 350'.

Figure 13:
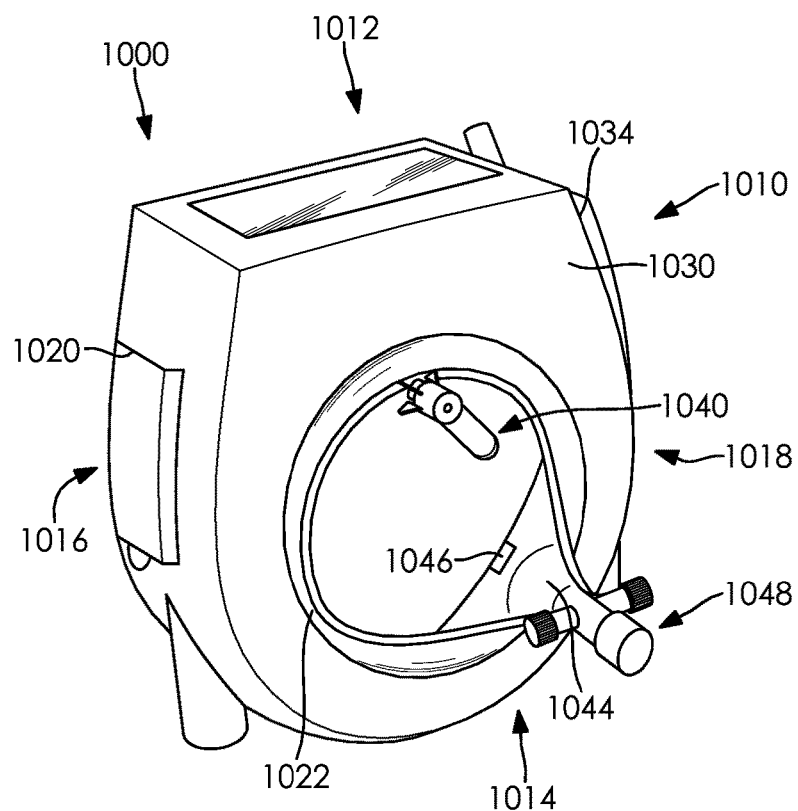
FIG. 13 is a perspective view of a second example device for extracorporeal conditioning of blood.
Figure 14:
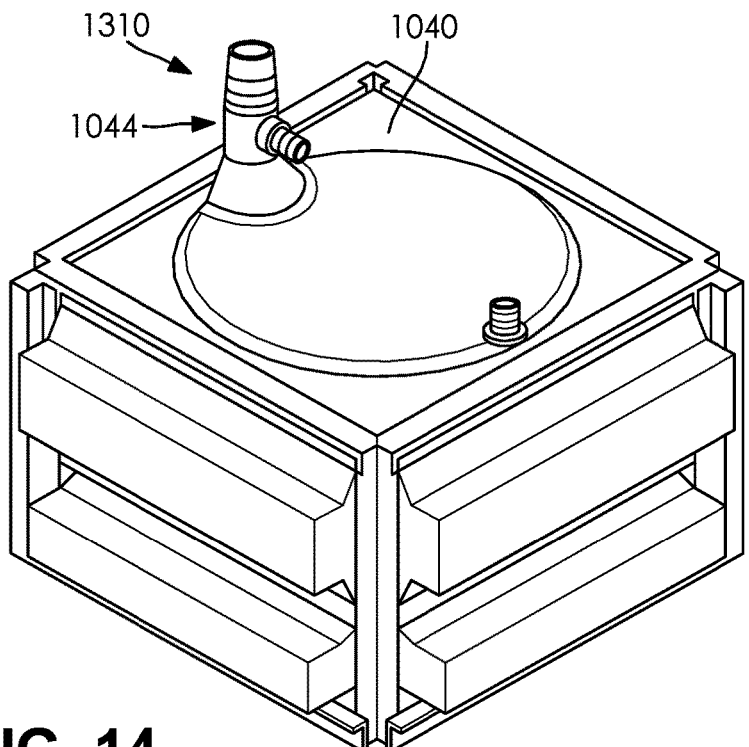
FIG. 14 is a perspective view of the conditioning module of the second example device.
Figure 15:
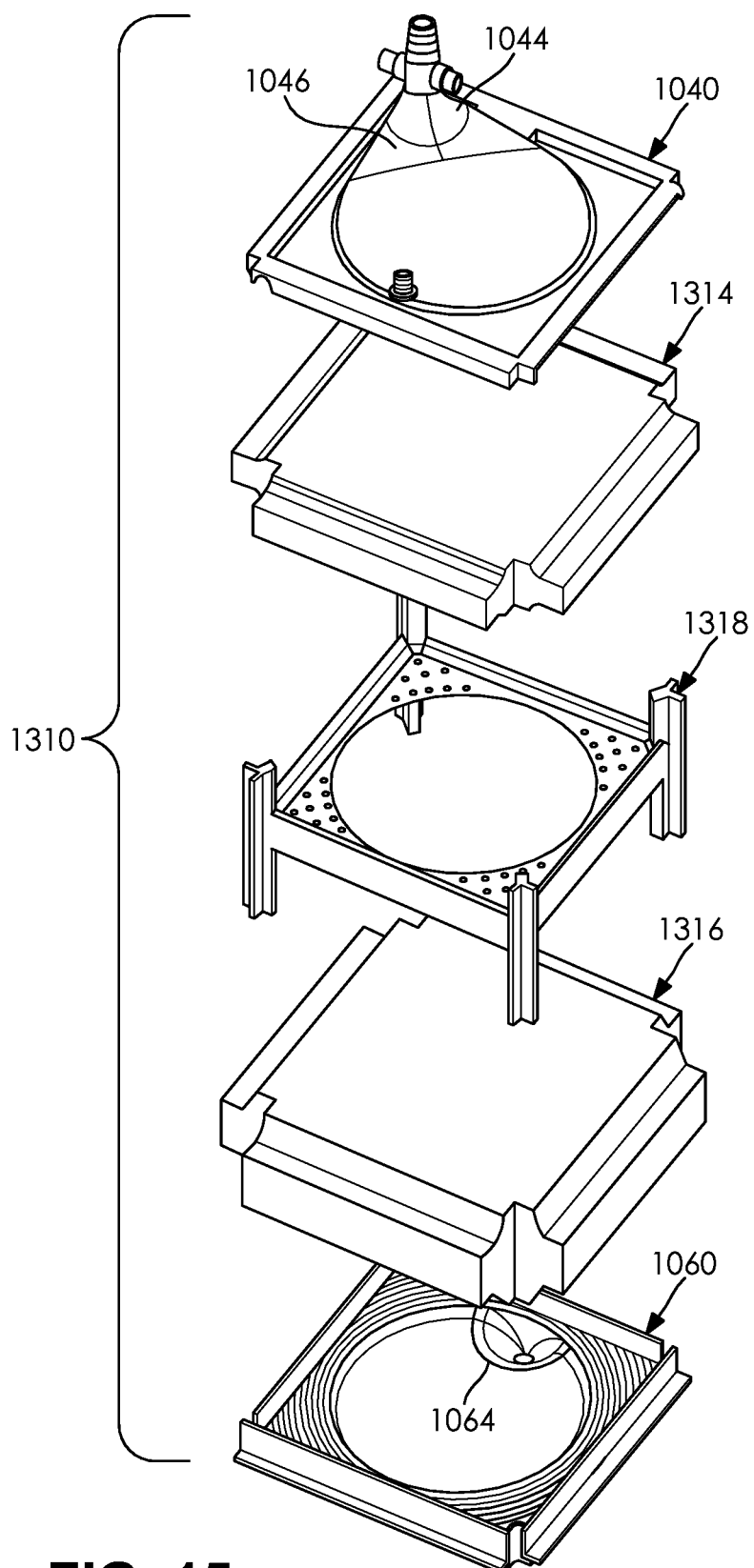
FIG. 15 is an exploded view of the conditioning module of the second example device.

Each of FIGS. 13, 14, and 15 illustrates a second example device 1000 for extracorporeal conditioning of blood, or an assembly or component thereof. FIG. 13 illustrates the device 1000 in a fully assembled form; each of FIGS. 14 and 15 illustrates an assembly or component of the device 1000 isolated, to a degree, from other portions of the device 1000.

The device 1000 has a housing 1010 that provides, generally, a first end 1012, a second end 1014, a first side 1016, and a second side 1018. The first end 1012 is generally opposite the second end 1014, and the first side 1016 is generally opposite the second side 1018. The housing 1010 has a first housing element 1020 and a second housing element 1030 that are attached to each other to form the housing 1010. It is noted that, while the illustrated embodiment includes first 1020 and second 1030 housing elements, a single unitary housing element could also be used in an embodiment.

The first housing element 1020 defines an opening 1022 and the second housing element 1030 defines an opening (not illustrated). The first 1020 and second 1030 housing elements cooperatively define an interior chamber 1034.

An inlet cover 1040 is disposed in the opening 1022 of the first housing element 1020. As best illustrated in FIG. 13, the inlet cover 1040 spans across the opening 1022 of the first housing element 1020. The inlet cover 1040 defines a window 1042 that allows visual observation of fluid flowing through the inlet cover 1040 within the interior chamber 1034 of the device 1000. Also, the inlet cover 1040 defines structure that provides fluid access to components disposed within the interior chamber 1034 of the device 1000, such as conditioning module 1310. As best illustrated in FIG. 13, the inlet cover 1040 defines an integrally formed inlet 1044 that provides fluid communication between internal chamber defined by the conditioning module 310 and the environment external to the device 1000, which can include an attached fluid supply line, such as in an extracorporeal blood circulation circuit. A seal can be included along the perimeter of the opening 1022 where the inlet cover 1040 interfaces with the first housing element 1020.

The inlet 1044 has a flow path that is linear at one end and partially circumferential at the other end. Thus, similar to the first example device 100, the port 1048 defines a linear flow path that gradually transitions to a partial circumferential flow path 1046 in the portion of the inlet 1044 that is disposed immediately adjacent the interior chamber 1034 of the device 100. In this embodiment, though, the portion of the flow path that is linear extends along an axis that is tangential to, or substantially tangential to, the portion of the flow path that is partially circumferential. Also in this embodiment, the portion of the flow path that is partially circumferential is partially spherical. That is, the portion of the flow path that is circumferential defines a portion of a hypothetical sphere. Also in this example, the portion of the flow path that is linear extends along an axis that is tangential to, or substantially tangential to, the hypothetical sphere of which the partially circumferential portion is a portion.

Figure 16A:
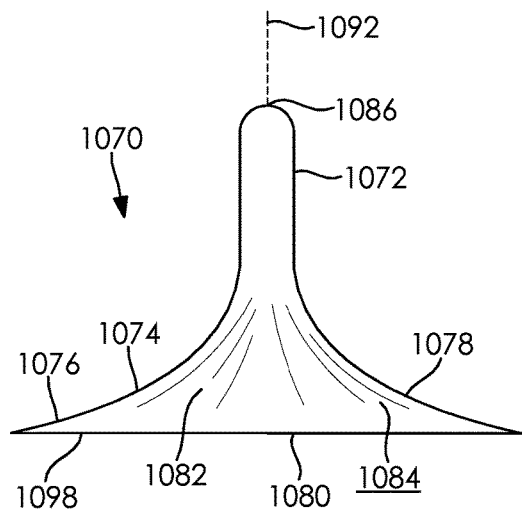
FIG. 16A is a front view of an inlet insert of the second example device.
Figure 16B:
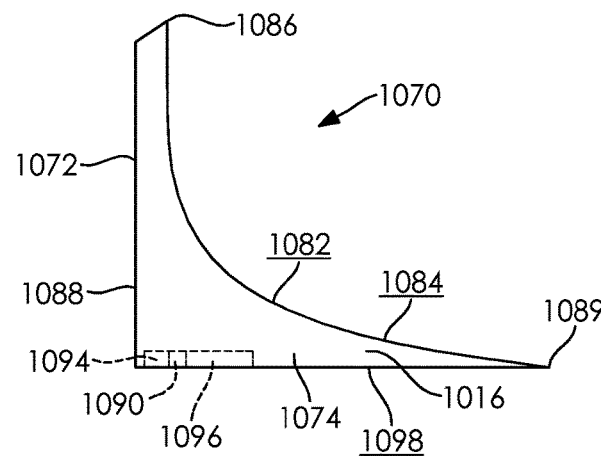
FIG. 16B is an elevation view of the inlet insert illustrated in FIG. 16A.
Figure 16C:
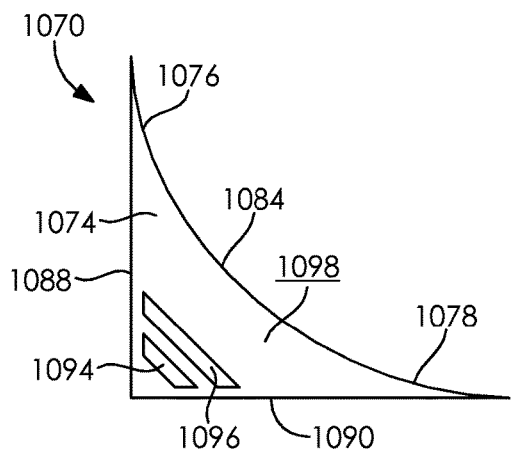
FIG. 16C is a bottom view of the inlet insert illustrated in FIG. 16A.
Figure 16D:
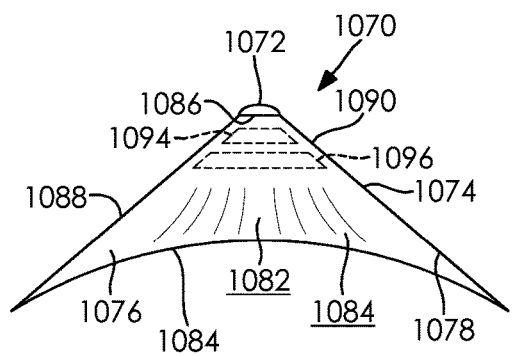
FIG. 16D is a top view of the inlet insert illustrated in FIG. 16A.

FIGS. 16A, 16B, 16C, and 16D illustrate an inlet insert 1070 that is disposed within the inlet cover 1040 and that provides a surface for transitioning fluid flow from the inlet 1044 to the internal chamber defined by the conditioning module 310. The inlet insert 1070 has a stem 1072 and a base 1074 having first 1076 and second 1078 arms. The base has a curvilinear edge 1080 extending between the first 1076 and second 1078 arms. The inlet insert 1070 also has an interior surface 1082 that defines a sloped surface 1084 extending from the curvilinear edge 1080 to the tip 1086 of the stem 1072. The inlet insert 1070 also defines first 1088 and second 1090 external surfaces that lie on planes that intersect each other along a longitudinal axis 1092 of the stem 1072. The external surfaces 1088, 1090 can lie on planes that intersect each other at any suitable angle. In the illustrated embodiment, the external surfaces 1088, 1090 lie on planes that intersect each other at an orthogonal or substantially orthogonal angle, which is considered advantageous for positioning the inlet insert 1070 within the inlet 1044 and inlet cover 1040. As best illustrated in FIG. 16C, the inlet insert 1070 defines first 1094 and second 1096 recesses on the bottom surface 1098. The recesses 1094, 1096 are sized and configured to interact with potting material in the final assembly of the device 1000. While the illustrated inlet insert 1070 has two recesses 1094, 1096, it is understood that any suitable number of recesses can be included in an inlet insert according to a particular embodiment.

Sloped surface 1084 can have any suitable configuration. In the illustrated embodiment, sloped surface 1084 has a substantially partial spherical surface, which the inventors have determined provides beneficial fluid flow properties as fluid moves through the inlet 1044 and into the interior chamber 1034 of the device 1000. Also, the sloped surface 1084 is smooth and free of structural interruptions.

The inlet insert 1070 can be integrally formed with the inlet cover 1040. The inventors have determined, though, that it is advantageous to fabricate the inlet insert 1070 as a separate structure that is ultimately secured to the inlet cover 1040 at least because this approach avoids the presence of hard angles within the flow path, which could ultimately impact the performance of the device 1000. If made as a separate structure, the inlet insert 1070 in an embodiment can be attached to the inlet cover 1040 using any conventional technique or means for attachment, including adhesives and the like.

An outlet cover 1060 is disposed in the opening (not illustrated) of the second housing element 1030. The outlet cover 1060 spans across the opening of the second housing element 1030. The outlet cover 1060 defines a window that allows visual observation of fluid flowing out of the components disposed within the interior chamber 1034 of the device 1000, such as conditioning module 1310. The outlet cover 1060 defines structure that provides fluid egress from components disposed within the interior chamber 1034 of the device 1000, such as conditioning module 1310. As best illustrated in FIG. 15, the outlet cover 1060 defines an integrally formed outlet 1064 that provides fluid communication between the internal chamber defined by the conditioning module 1310 and the environment external to the device 1000, which can include an attached fluid supply line, such as in an extracorporeal blood circulation circuit. A seal can be included along the perimeter of the opening 1032 where the outlet cover 1060 interfaces with the second housing element 1030.

A conditioning module 1310 is disposed within the interior chamber 1034 of the device 1000. The conditioning module 1310 provides the structure that enables fluid flowing through the device 1000 to interface with other fluids flowing through fluidly separate fluid flow pathways defined by the device 1000 and/or conditioning module 1310 to achieve a desired conditioning of the fluid, such as gas flowing through a gas pathway and heat exchange fluid flowing through a heat exchange pathway, for example.

Figure 17A:
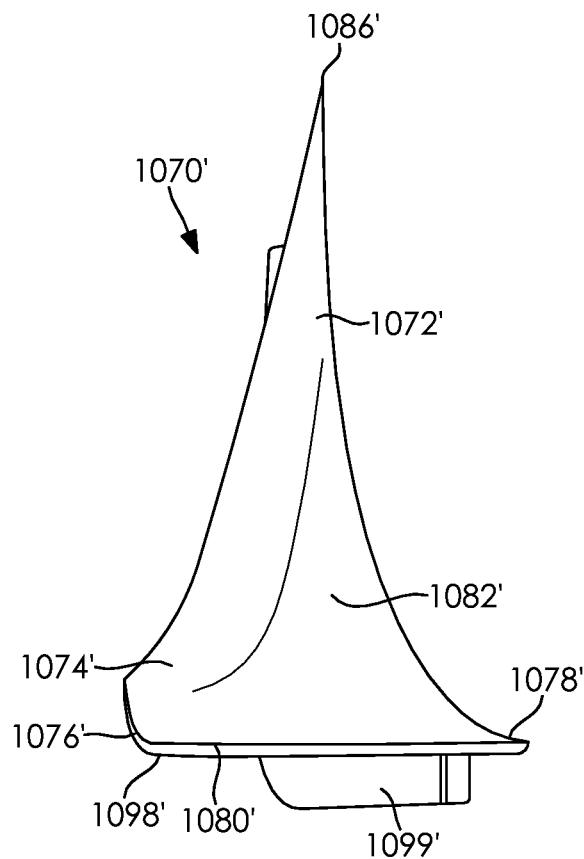
FIG. 17A is an isolated view of an alternative inlet insert.
Figure 17B:
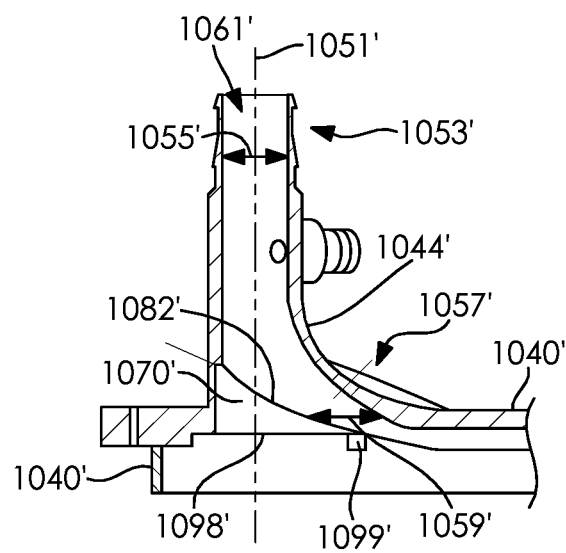
FIG. 17B is a sectional view, partially broken away, of an inlet cover and the inlet insert illustrated in FIG. 17A.
Figure 17C:
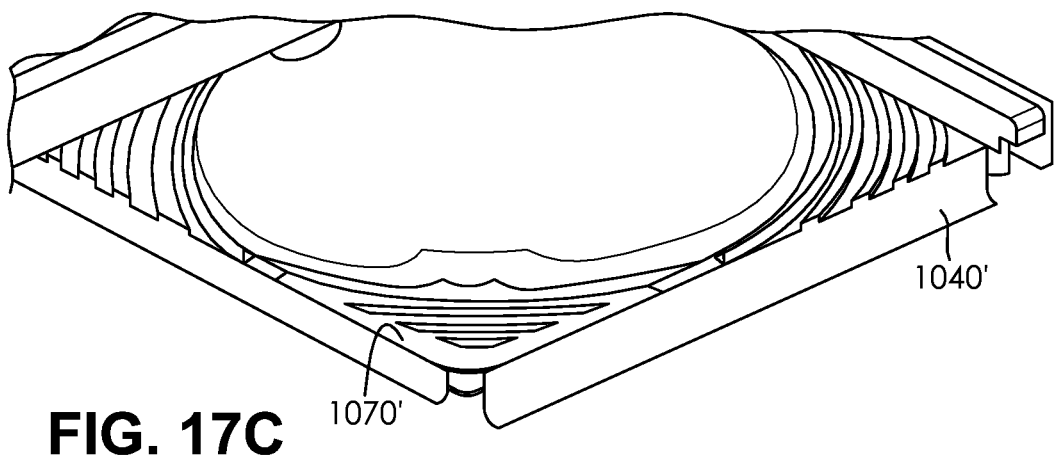
FIG. 17C is a bottom view of an inlet cover and the inlet insert illustrated in FIG. 17A.
Figure 17D:
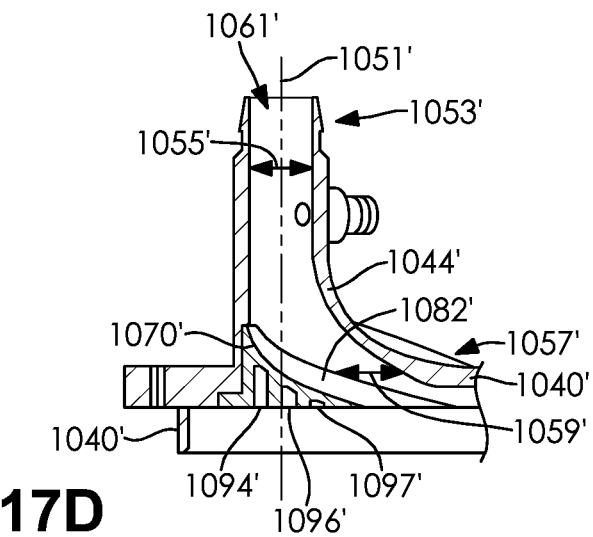
FIG. 17D is another sectional view, partially broken away, of the inlet cover and inlet insert illustrated in FIG. 17A.
Figure 17E:
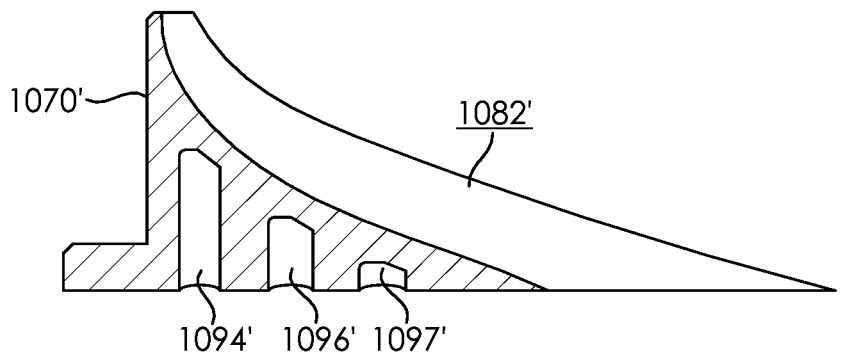
FIG. 17E is a magnified sectional view of the inlet insert illustrated in FIG. 17D, isolated from the inlet cover.
Figure 17F:
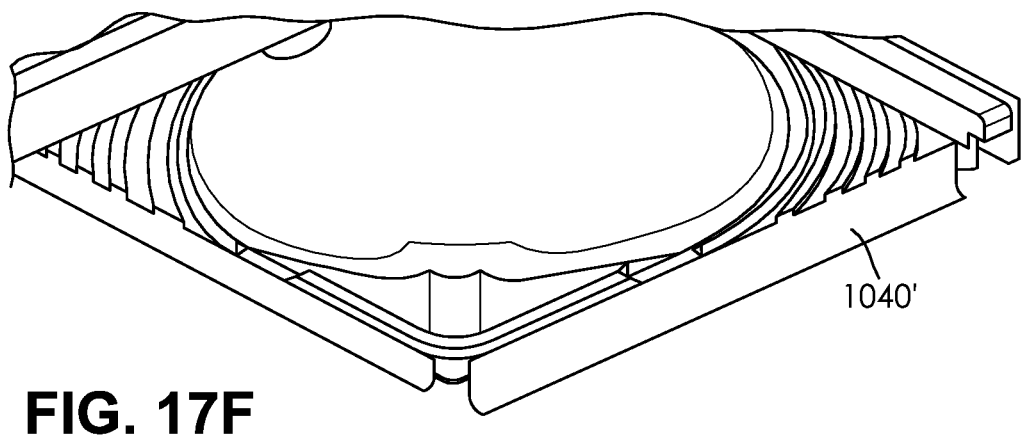
FIG. 17F is a bottom view of an inlet cover isolated from the inlet insert.

FIGS. 17A, 17B, 17C, 17D, and 17E illustrates an alternative inlet insert 1070' suitable for use with devices according to the invention. The inlet insert 1070' is similar to the inlet insert 1070 described above, except as detailed below. Inlet insert 1070' is disposed within the inlet cover 1040' and provides a surface for transitioning fluid flow from the inlet 1044' to the internal chamber defined by the conditioning module. The inlet insert 1070' has a stem 1072' and a base 1074' having first 1076' and second 1078' arms. The base has a curvilinear edge 1080' extending between the first 1076' and second 1078' arms. The inlet insert 1070' also has an interior surface 1082' that defines a sloped surface 1084' extending from the curvilinear edge 1080' to the tip 1086' of the stem 1072'. As best illustrated in FIGS. 17D and 17E, the inlet insert 1070' defines first 1094', second 1096', and third 1097' recesses on the bottom surface 1098'. In this example, inlet insert 1070' defines a rib 1099' that extends away from the bottom surface 1098'.

As best illustrated in FIGS. 17B and 17D, inlet insert 1070' cooperates with inlet cover 1040' and inlet 1044' to define different internal heights for the fluid inlet and the flow path extending therethrough. The fluid inlet 1044' extends along a first axis 1051' that is substantially perpendicular to a plane containing the inlet cover 1040', and also to a plane containing the plurality of fiber mats associated with the device that includes the inlet cover 1040' (not illustrated in the figures). A first end 1053' of the fluid inlet 1044' has a first internal height 1055' perpendicular to the first axis 1051' and a second end 1057' of the fluid inlet 1044' has a second internal height 1059' perpendicular to the first axis 1051'. The second internal height 1059' is less than the first internal height 1055'. The sloped surface 1084' defines a curvilinear surface that transitions the inner lumen 1061' of the fluid inlet 1044' from the first internal height 1055' to the second internal height 1059'. This structural configuration is considered advantageous at least because the relative differences between the internal heights 1055', 1059' provide desirable fluid flow characteristics for fluid flowing through the inlet 1044' and into the conditioning module contained within a device according to an embodiment.

As best illustrated in FIG. 15, the conditioning module 1310 has a first chamber 1314 and a second chamber 1316. A frame 1318 is disposed between the first 1314 and second 1316 chambers and substantially fixes the relative positions of the chambers 1314, 1316. In the illustrated embodiment, the frame 1318 is a separate component that is assembled with the first 1314 and second 1316 chambers. It is noted, though, that frame could be integrally formed with the first 1314 and second 1316 chambers in an embodiment. If a separate frame is used, such as frame 1318, the frame is advantageously attached to the first 1314 and second 1316 chambers, such as with application of an appropriate sealant, formation of an a suitable joint, such as a weld joint, or through other suitable means for attaching members to each other. The inlet cover 1040 is secured to the frame 1318 and disposed adjacent the first chamber 1314. The outlet cover 1060 is secured to the frame 1318 and disposed adjacent the second chamber 1316.

Figure 18:
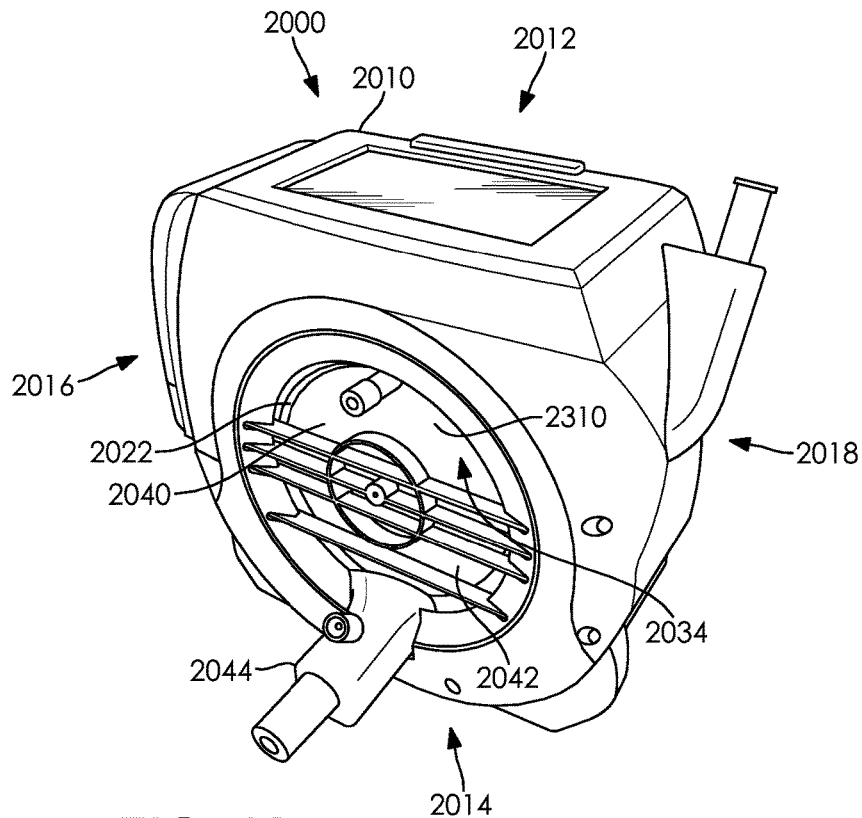
FIG. 18 is a perspective view of a third example device for extracorporeal conditioning of blood.
Figure 19:
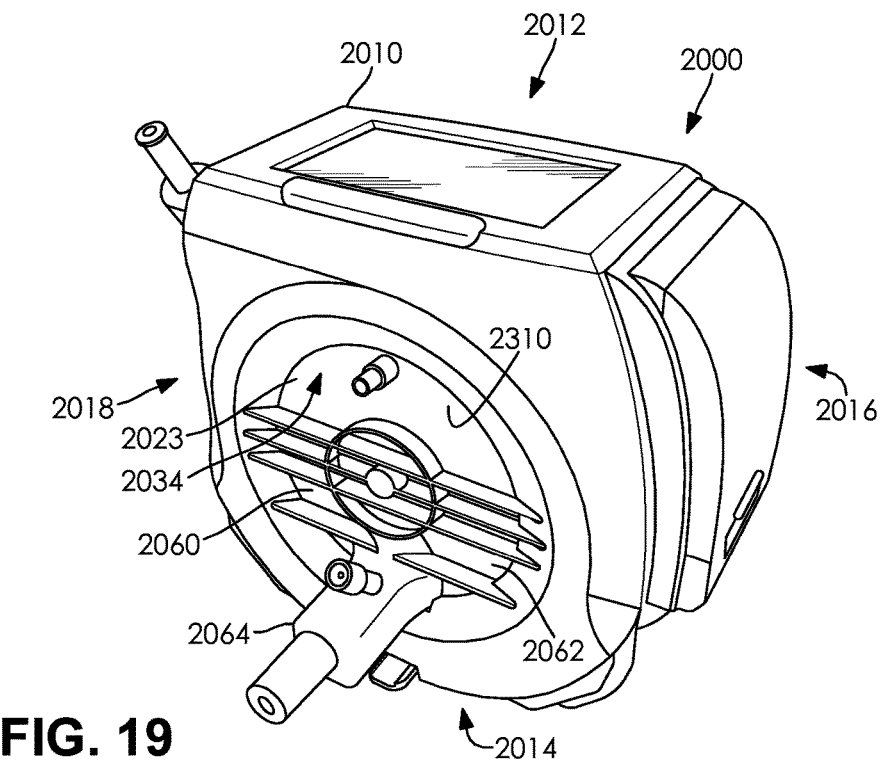
FIG. 19 is another perspective view of the third example device for extracorporeal conditioning of blood.
Figure 20:
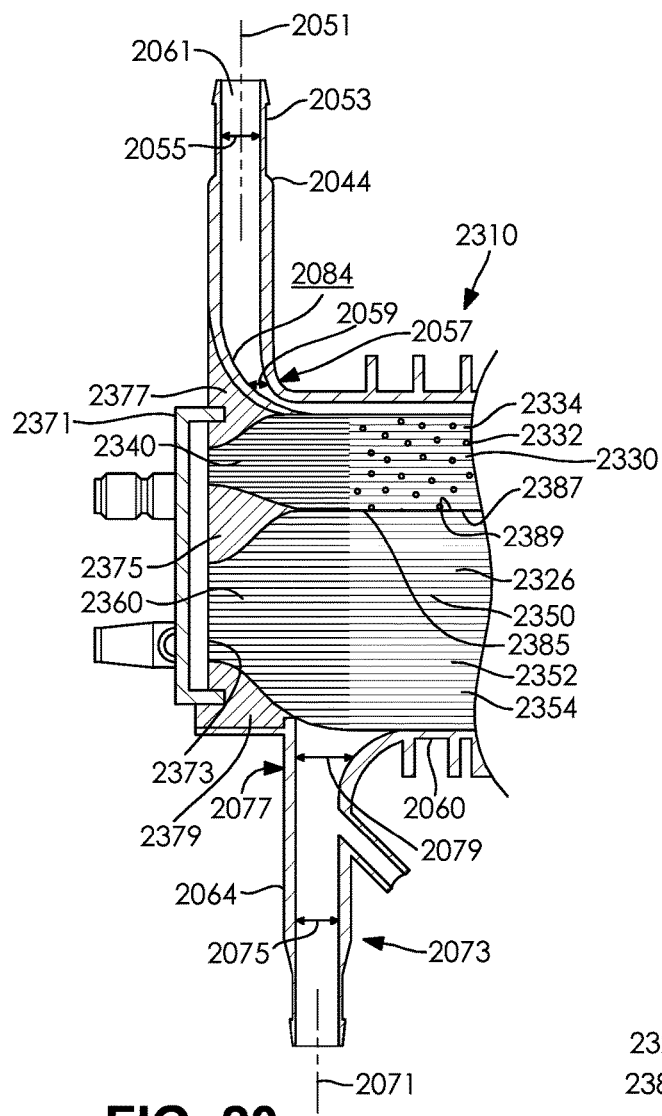
FIG. 20 is a sectional view, partially broken away, of the conditioning module of the third example device.
Figure 21:
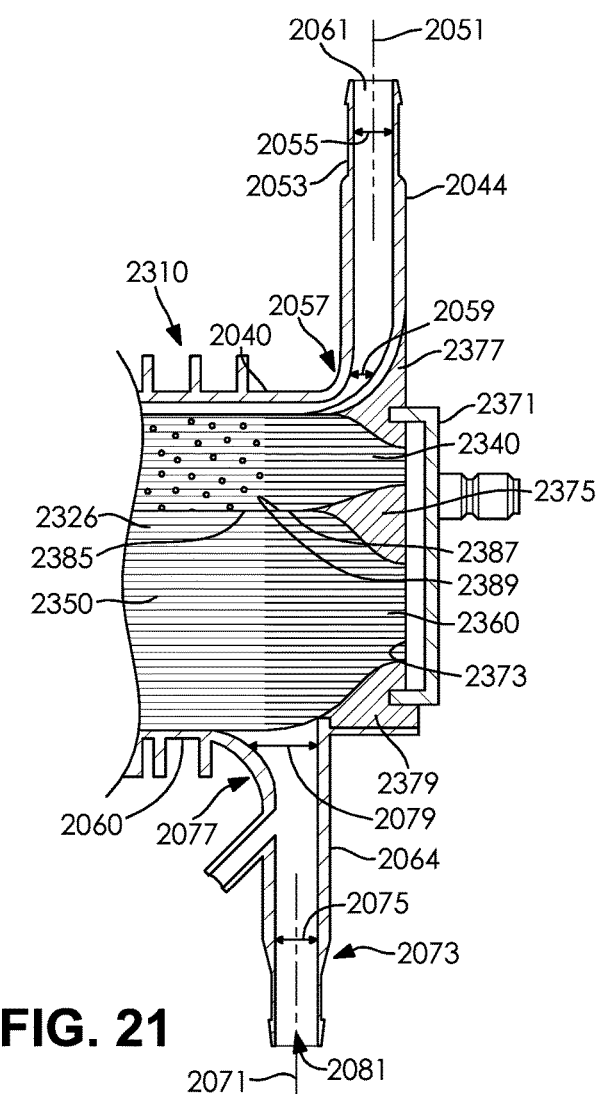
FIG. 21 is another sectional view, partially broken away, of the conditioning module of the third example device.

Each of FIGS. 18, 19, 20, and 21 illustrates a third example device 2000 for extracorporeal conditioning of blood, or an assembly or component thereof. FIGS. 18 and 19 illustrate the device 2000 in a fully assembled form; FIGS. 20 and 21 illustrate a partial section of the conditioning module 2310 of the device 2000.

The device 2000 is similar to devices 100, 1000 described above, except as detailed below. The device 2000 has a housing 2010 that provides, generally, a first end 2012, a second end 2014, a first side 2016, and a second side 2018. The first end 2012 is generally opposite the second end 2014, and the first side 2016 is generally opposite the second side 2018. The housing 2010 defines an interior chamber 2034 and openings 2022, 2023 to the interior chamber 2034.

Conditioning module 2310 is disposed within the interior chamber 2034 of the housing such that inlet cover 2040 is positioned within opening 2022 and outlet cover 2060 is positioned within opening 2023. The inlet cover 2040 defines a window 2042 that allows visual observation of fluid flowing through the inlet cover 2040 to the internal module chamber 2373 defined by the conditioning module 2310. Also, the inlet cover 2040 defines structure that provides fluid access to the internal module chamber 2373 defined by the conditioning module 2310. The inlet cover 2040 defines an integrally formed inlet 2044 that provides fluid communication between the internal module chamber 2373 defined by the conditioning module 2310 and the environment external to the device 2000, which can include an attached fluid supply line, such as in an extracorporeal blood circulation circuit. The outlet cover 2060 defines a window 2062 that allows visual observation of fluid flowing through the outlet cover 2040 from the internal module chamber 2373 defined by the conditioning module 2310. Also, the outlet cover 2060 defines structure that provides fluid egress from the internal module chamber 2373 defined by the conditioning module 2310. The outlet cover 2060 defines an integrally formed outlet 2064 that provides fluid communication between the internal module chamber 2373 defined by the conditioning module 2310 and the environment external to the device 2000, which can include an attached fluid egress line, such as in an extracorporeal blood circulation circuit. The inlet cover 2040 and outlet cover 2060 are positioned such that the inlet 2044 and outlet 2064 are both generally positioned on the second end 2014 of the device 2000. In the illustrated embodiment, the longitudinal axes of the inlet 2044 and outlet 2064 are coplanar.

As best illustrated in FIGS. 20 and 21, the conditioning module 2310 has an external frame 2371 to which the inlet cover 2040 and outlet cover 2060 are secured. The external frame 2371, inlet cover 2040, and outlet cover 2060 cooperatively define the internal module chamber 2373. The conditioning module 2310 defines a passageway 2326 that extends from the inlet cover 2040, through the internal module chamber 2373 and to the outlet cover 2060. The passageway 2326 is in fluid communication with the inlet 2044 of the inlet cover 2040 and the outlet 2064 of the outlet cover 2060. Thus, the passageway 2326 extends through the conditioning module 2310, allowing fluid to flow through the internal module chamber 2373 of the conditioning module 2310. The passageway 2326 is bounded by potting material 2340 and 2360, which has a circumferential border within the internal module chamber 2373 to give the passageway 2326 a substantially circular cross-sectional shape. In use, fluid flows through the passageway 2326, and through the internal module chamber 2373 of the conditioning module 2310 from the inlet 2044 to the outlet 2064.

First 2330 and second 2350 fiber assemblies are disposed within the internal module chamber 2373. The first fiber assembly 2330 includes first 2332 and second 2334 pluralities of fiber mats arranged such that the fibers of the first plurality of mats 2332 are arranged substantially orthogonally to the fibers of the fiber mats of the second plurality of fiber mats 2334. Potting material 2340 is disposed throughout the peripheral edge of the first fiber assembly 2330 to create a circumferential seal that defines a flow path through the first fiber assembly 2330 that has a substantially circular cross-sectional shape. The flow path defined by the potting material 2340 comprises a portion of the passageway 2326. The second fiber assembly 2350 includes third 2352 and fourth 2354 pluralities of fiber mats arranged such that the fibers of the third plurality of mats 2352 are arranged substantially orthogonally to the fibers of the fiber mats of the fourth plurality of fiber mats 2354. Potting material 2360 is disposed throughout the peripheral edge of the second fiber assembly 2350 to create a circumferential seal that defines a flow path through the second fiber assembly 2350 that has a substantially circular cross-sectional shape. The flow path defined by the potting material 2360 comprises a portion of the passageway 2326.

The first 2330 and second 2350 fiber assemblies are in direct contact with each other—there is no structural member disposed between the first 2330 and second 2350 fiber assemblies within the passageway 2326. A terminal mat 2387 of the first fiber assembly 2330 is in direct contact with an adjacent terminal mat 2389 of the second fiber assembly 2350 along the entire interface 2385 between the first 2330 and second 2350 fiber assemblies within the passageway 2326. There is no other structure disposed between the first 2330 and second 2350 fiber assemblies within the passageway 2326 bounded by potting 2340, 2360.

Separating member 2375 extends into the internal module chamber 2373 along internal surfaces of the external frame 2371 and can extend entirely around the internal module chamber 2373 to provide a circumferential separating member. The separating member 2375 extends into and partially separates potting 2340 and potting 2360, forcing the peripheral edges of the innermost fiber mats of the first fiber assembly 2330 toward the inlet cover 2040 and peripheral edges of the innermost fiber mats of the second fiber assembly 2350 toward the outlet cover 2060. External frame 2371 also defines an inlet projection 2377 and an outlet projection 2379, each of which extends inwardly into the internal module chamber 2373. The inlet projection 2377 forces the peripheral edges of the fiber mats of the first fiber assembly 2330 that are relatively close to the inlet cover 2140 away from the underside of the inlet cover 2040. Similar, the outlet projection 2379 forces the peripheral edges of the fiber mats of the second fiber assembly 2350 that are relatively close to the outlet cover 2160 away from the underside of the outlet cover 2060. Similar to the separating member 2375, each of the inlet projection 2377 and the outlet projection 2379 extends along internal surfaces of the external frame 2371 and can extend entirely around the internal module chamber 2373 to provide a circumferential projection if desired.

The separating member 2375, inlet projection 2377, and outlet projection 2379 cooperate to partially separate the peripheral edge of the first fiber assembly 2330 from the peripheral edge of the second fiber assembly 2350 and to compress the peripheral edges of the fiber mats of the first 2330 and second 2350 fiber assemblies to a taper having a shortened height within the width of the respective potting 2340, 2360.

As best illustrated in FIGS. 20 and 21, inlet 2044 extends along a first axis 2051 that is substantially perpendicular to a plane containing the inlet cover 2040, and also to a plane containing the first 2030 and second 2050 fiber assemblies. The inlet 2044 has an inner lumen 2061, a first end 2053 having a first internal height 2055 perpendicular to the first axis 2051 and a second end 2057 having a second internal height 2059 perpendicular to the first axis 2051. The second internal height 2059 is less than the first internal height 2055. Sloped surface 2084 defines a curvilinear surface that transitions the inner lumen 2061 of the fluid inlet 2044 from the first internal height 2055 to the second internal height 2059.

Also as best illustrated in FIGS. 20 and 21, the inner lumen 2061 of the inlet 2044 has a reduced internal height 2059 at the second end 2057 where the inlet 2044 interfaces with the first fiber assembly 2030, as compared to the internal height 2055 of the inner lumen of the inlet 2044 at its opposite first end 2053.

Outlet 2064 extends along a second axis 2071 that is substantially perpendicular to a plane containing the outlet cover 2060, and also to a plane containing the first 2030 and second 2050 fiber assemblies. The second axis 2071 is coplanar with the first axis 2051. In contrast to the inner lumen 2061 of the inlet 2044, the inner lumen 2081 of the outlet 2064 has a greater internal height 2079 at its second end 2077 where the outlet 2064 interfaces with the second fiber assembly 2050, as compared to the internal height 2075 of the inner lumen of the outlet 2064 at its opposite first end 2073.

Figure 22:
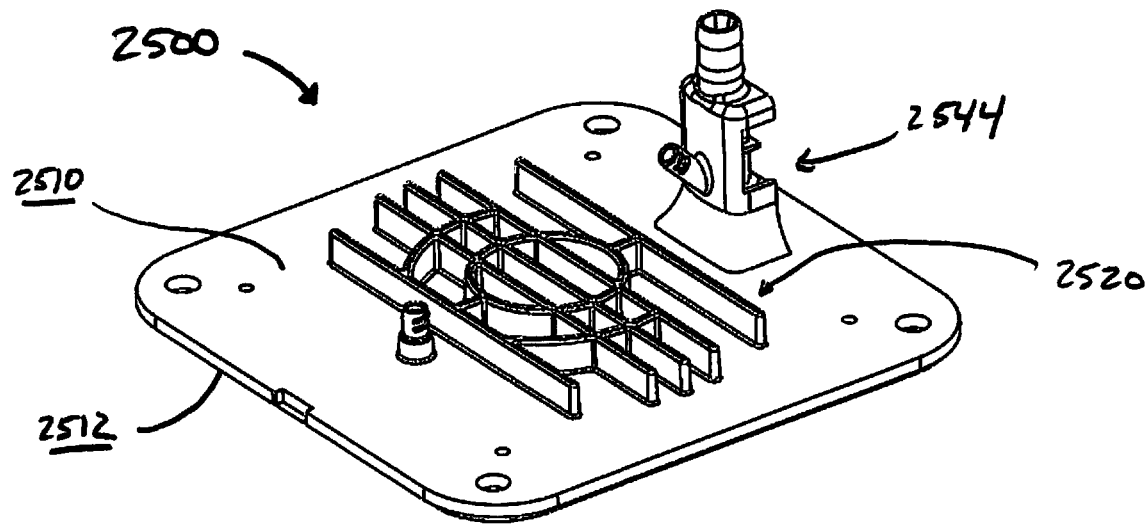
FIG. 22 is a perspective view of an alternative inlet cover.
Figure 23:
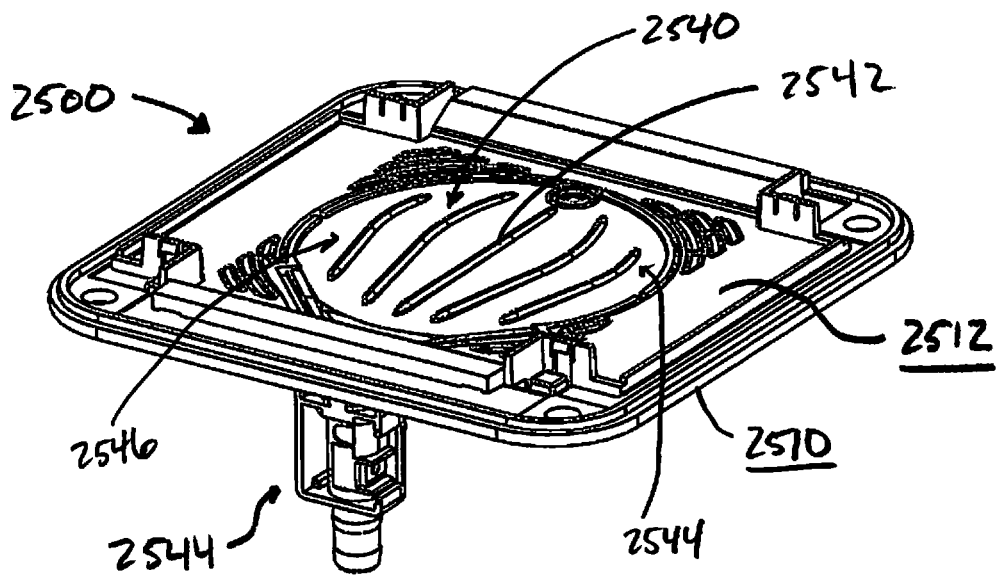
FIG. 23 is another perspective view of the inlet cover illustrated in FIG. 22.
Figure 24:
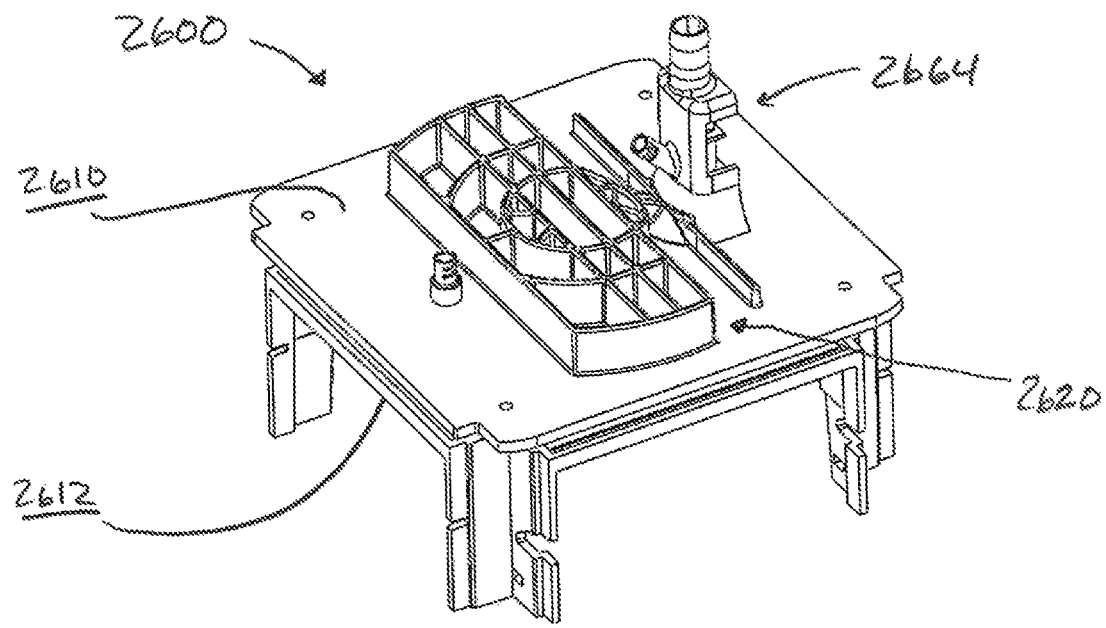
FIG. 24 is a perspective view of an alternative outlet cover.
Figure 25:
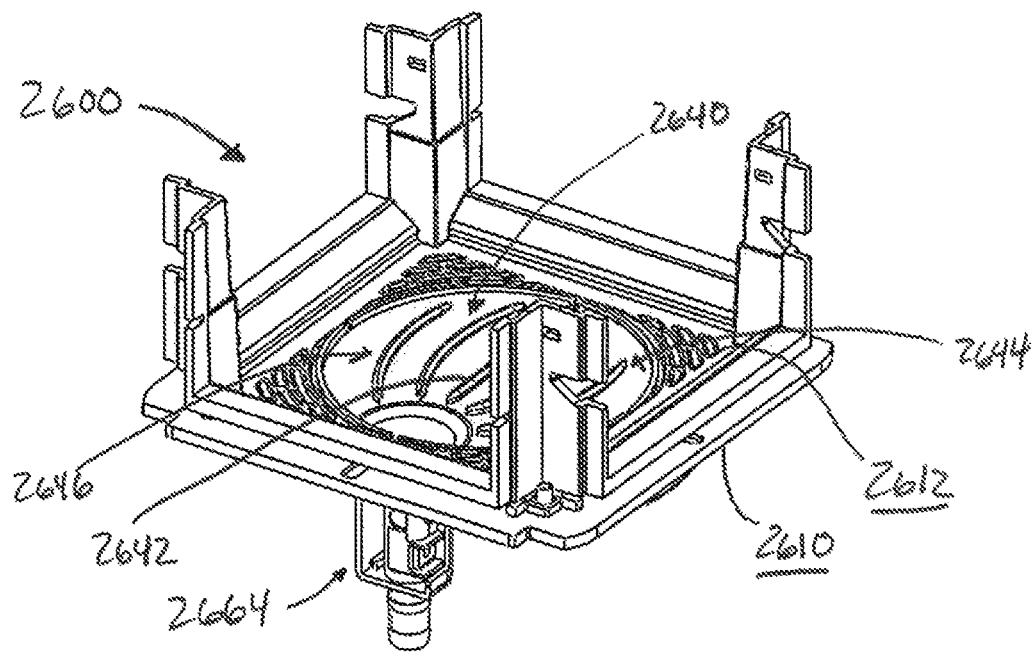
FIG. 25 is another perspective view of the outlet cover illustrated in FIG. 24.

FIGS. 22 and 23 illustrate an alternative inlet cover 2500 that is suitable for use with device 2000 and devices according to other embodiments. FIGS. 24 and 25 illustrate an alternative inlet cover 2500 that is suitable for use with device 2000 and devices according to other embodiments.

The inlet cover 2500 has external 2510 and internal 2512 surfaces. Fluid inlet 2544 extends away from the external surface 2510 and defines an internal lumen and other structure similar to the fluid inlet 2044 described above. In an assembled device, the external surface 2510 is positioned on the outside of the internal module chamber defined by the conditioning module that includes the inlet cover 2500. Thus, the external surface 2510 does not contact elements that are positioned within the internal module chamber, such as fiber assemblies and/or potting. As best illustrated in FIG. 22, external surface 2510 defines a plurality of outwardly extending ribs 2520 that can facilitate securement of the inlet cover 2500, and indeed a conditioning module that includes the inlet cover 2500, to the housing of a device according to an embodiment. While the plurality of outwardly extending ribs 2520 are illustrated in a specific arrangement, shape, and number, it is understood that a device according to an embodiment that includes an inlet cover with a plurality of outwardly extending ribs can include any suitable arrangement, shape, and number of ribs in the plurality of outwardly extending ribs. Skilled artisans will be able to select a suitable arrangement, shape, and number of ribs for an inlet cover in a device according to a particular embodiment based on various considerations, including the structure of the housing elements of the device in which the inlet cover will be used.

In an assembled device, the internal surface 2510 is positioned on the inside of the internal module chamber defined by the conditioning module that includes the inlet cover 2500. Thus, the internal surface 2510 directly faces elements that are positioned within the internal module chamber, such as fiber assemblies and/or potting.

As best illustrated in FIG. 23, a plurality of vanes 2540 extends away from the internal surface 2512. Each vane is an elongate projection that extends away from the internal surface 2512. In an assembled device, each vane of the plurality of vanes extends away from the internal surface 2512 toward the elements that are positioned within the internal module chamber, such as fiber assemblies and/or potting. Indeed, it is considered advantageous to configure each vane of the plurality of vanes 2540 to have a height that is sufficient for the vane to be in direct contact with a fiber assembly within the internal module chamber of a conditioning module. It is considered particularly advantageous to configure each vane of the plurality of vanes 2540 to be in direct contact with a fiber assembly along the entire length of the vane. Vanes constructed in this manner structurally urge the fiber assemblies within the internal module chamber to maintain a desired configuration and limits the development of less desirable configurations, such as an undulating or pillowing configuration of the fiber mats in the fiber assembly.

Any suitable number of vanes can be included in an inlet cover that includes vanes, and the illustrated embodiment is only one example of a suitable number. The inventors have determined that the inclusion of an odd number of vanes, such as 3, 5, 7, or 9 vanes is advantageous as it allows for the inclusion of a linear or substantially linear central vane, such as vane 2542, flanked by matching sets of lateral vanes 2544, 2546 that curve outwardly along their length. The inventors have also determined, though, that omission of a central vane can provide desirable fluid flow through a conditioning module that includes the inlet cover 2500. For example, inclusion of matching sets of lateral vanes 2544, 2546, with omission of central vane 2542, is considered a suitable arrangement of a vanes for an inlet cover according to a particular embodiment.

The inlet cover 2600 has external 2610 and internal 2612 surfaces. Fluid outlet 2664 extends away from the external surface 2610 and defines an internal lumen and other structure similar to the fluid outlet 2064 described above. In an assembled device, the external surface 2610 is positioned on the outside of the internal module chamber defined by the conditioning module that includes the outlet cover 2600. Thus, the external surface 2610 does not contact elements that are positioned within the internal module chamber, such as fiber assemblies and/or potting. As best illustrated in FIG. 24, external surface 2610 defines a plurality of outwardly extending ribs 2620 that can facilitate securement of the outlet cover 2600, and indeed a conditioning module that includes the outlet cover 2600, to the housing of a device according to an embodiment. While the plurality of outwardly extending ribs 2620 are illustrated in a specific arrangement, shape, and number, it is understood that a device according to an embodiment that includes an outlet cover with a plurality of outwardly extending ribs can include any suitable arrangement, shape, and number of ribs in the plurality of outwardly extending ribs. Skilled artisans will be able to select a suitable arrangement, shape, and number of ribs for an outlet cover in a device according to a particular embodiment based on various considerations, including the structure of the housing elements of the device in which the outlet cover will be used.

In an assembled device, the internal surface 2612 is positioned on the inside of the internal module chamber defined by the conditioning module that includes the outlet cover 2600. Thus, the internal surface 2612 directly faces elements that are positioned within the internal module chamber, such as fiber assemblies and/or potting.

As best illustrated in FIG. 25, a plurality of vanes 2640 extends away from the internal surface 2612. Each vane is an elongate projection that extends away from the internal surface 2612. In an assembled device, each vane of the plurality of vanes extends away from the internal surface 2612 toward the elements that are positioned within the internal module chamber, such as fiber assemblies and/or potting. Indeed, it is considered advantageous to configure each vane of the plurality of vanes 2640 to have a height that is sufficient for the vane to be in direct contact with a fiber assembly within the internal module chamber of a conditioning module. It is considered particularly advantageous to configure each vane of the plurality of vanes 2640 to be in direct contact with a fiber assembly along the entire length of the vane. Vanes constructed in this manner structurally urge the fiber assemblies within the internal module chamber to maintain a desired configuration and limits the development of less desirable configurations, such as an undulating or pillowing configuration of the fiber mats in the fiber assembly.

Any suitable number of vanes can be included in an outlet cover that includes vanes, and the illustrated embodiment is only one example of a suitable number. The inventors have determined that the inclusion of an odd number of vanes, such as 3, 5, 7, or 9 vanes is advantageous as it allows for the inclusion of a linear or substantially linear central vane, such as vane 2642, flanked by matching sets of lateral vanes 2644, 2646 that curve outwardly along their length. The inventors have also determined, though, that omission of a central vane can provide desirable fluid flow through a conditioning module that includes the outlet cover 2600. For example, inclusion of matching sets of lateral vanes 2644, 2646, with omission of central vane 2642, is considered a suitable arrangement of a vanes for an outlet cover according to a particular embodiment.

Figure 26:
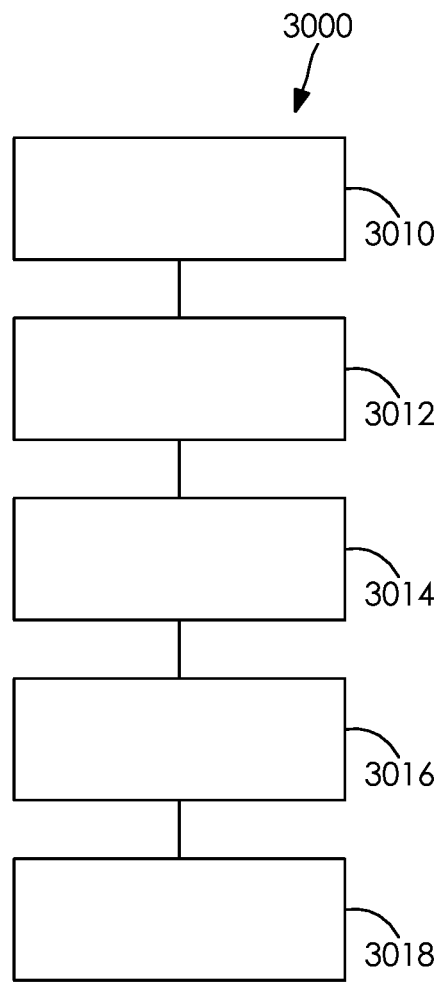
FIG. 26 is schematic representation of a method of manufacturing a fiber assembly suitable for use in a device for extracorporeal conditioning of blood.

FIG. 26 is schematic representation of a method 3000 of manufacturing a fiber assembly suitable for use in a device for extracorporeal conditioning of blood. A first step 3010 comprises assembling a first fiber assembly comprising a first plurality of fiber mats and a second plurality of fiber mats such that fibers of the first plurality of fiber mats are arranged substantially orthogonally to the fibers of the fiber mats of the second plurality of fiber mats. A second step 3012 comprises cutting the first fiber assembly to form a fiber assembly precursor having a substantially square shape. A third step 3014 comprises placing the fiber assembly precursor into a cartridge adapted to be attached to a centrifuge to spin the fiber assembly precursor on its central axis. A fourth step 3016 comprises placing potting material into the cartridge. A fifth step 3018 comprises spinning the cartridge and fiber assembly precursor in the centrifuge to achieve a radial dispersion of the potting material throughout the peripheral edge of the fiber assembly precursor to form a fiber assembly in which the potting material forms a circumferential border and defines a flow path having a substantially circular cross-sectional shape.

Figure 27:
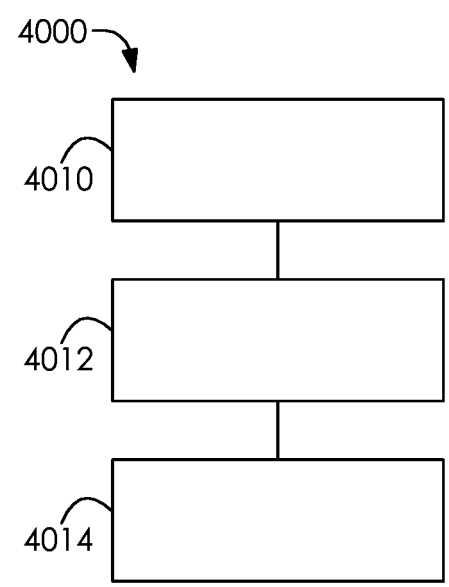
FIG. 27 is a schematic representation of a method of manufacturing a device for extracorporeal conditioning of blood.

FIG. 27 is a schematic representation of a method 4000 of manufacturing a device for extracorporeal conditioning of blood. A first step 4010 comprises performing the method 3000 illustrated in FIG. 26 and described above. A second step 4012 comprises placing the fiber assembly into a conditioning module that includes an inlet cover according to an example described herein and an outlet cover according to an example described herein. A third step 4014 comprises placing the conditioning module into an interior chamber cooperatively defined by first and second housing elements to form the device for extracorporeal conditioning of blood.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate the invention only and are not intended to limit the scope of the invention, which is to be given the full breadth of the appended claims and any and all equivalents thereof

We claim:

1. A device for extracorporeal conditioning of blood, comprising:
   a conditioning module comprising an external frame, an inlet cover, an outlet cover, and defining an internal chamber;
   a first fiber assembly disposed within the internal chamber and having a first peripheral edge;
   potting material disposed throughout the first peripheral edge to create a seal that defines a passageway through the first fiber assembly;
   a fluid inlet disposed on the inlet cover and defining a flow path having a first end defining an inlet opening and a second end adjacent the conditioning module and in fluid communication with the passageway, the flow path having a linear portion at the first end and a partial circumferential portion at the second end; and
   a fluid outlet disposed on the outlet cover, the fluid outlet having an outlet lumen in fluid communication with the passageway.

2. The device of claim 1, wherein the seal defined by the potting material is a circumferential seal such that the passageway has a substantially circular cross-sectional shape.

3. The device of claim 1, wherein the inlet opening is a circular opening.

4. The device of claim 3, wherein the second end of the fluid inlet defines a partial circumferential opening that opens to the internal chamber of the conditioning module.

5. The device of claim 1, wherein the fluid inlet has a lengthwise axis at the first end;
   wherein the fluid inlet has a first internal height measured along a first transverse axis disposed orthogonally to the lengthwise axis;
   wherein the fluid inlet has a second internal height measured along a second transverse axis disposed orthogonally to the lengthwise axis; and
   wherein the first and second internal heights are different.

6. The device of claim 5, wherein the first internal height is located at the first end of the flow path.

7. The device of claim 6, wherein the second internal height is located at the second end of the flow path.

8. The device of claim 7, wherein the first internal height is greater than the second internal height.

9. The device of claim 1, wherein the fluid inlet extends away from the conditioning module in a first direction; and
   wherein the fluid outlet extends away from the conditioning module in a second direction.

10. The device of claim 1, further comprising a sensor module disposed on the fluid inlet, the sensor module comprising one or more sensors individually configured to measure a property of fluid flowing through the fluid inlet.

11. The device of claim 10, wherein the one or more sensors comprises one or more of a pressure sensor, a temperature sensor, or an optical sensor.

12. The device of claim 1, wherein the linear portion of the flow path and the partial circumferential portion of the flow path lie in a same plane.

13. The device of claim 1, wherein the linear portion of the flow path extends along an axis that is tangential to the partial circumferential portion of the flow path.

14. A device for extracorporeal conditioning of blood, comprising:
   a conditioning module comprising an external frame, an inlet cover, an outlet cover, and defining an internal chamber;
   a first fiber assembly disposed within the internal chamber and having a first peripheral edge;
   potting material disposed throughout the first peripheral edge to create a circumferential seal that defines a passageway through the first fiber assembly having a substantially circular cross-sectional shape;
   a fluid inlet disposed on the inlet cover and defining a flow path having a first end defining an inlet opening and a second end adjacent the conditioning module and in fluid communication with the passageway, the flow path having a linear portion having a first internal height at the first end and a partial circumferential portion having a second internal height at the second end that is different from the first internal height; and
   a fluid outlet disposed on the outlet cover, the fluid outlet having an outlet lumen in fluid communication with the passageway.

15. The device of claim 14, wherein the inlet opening is a circular opening.

16. The device of claim 15, wherein the second end of the fluid inlet defines a partial circumferential opening that opens to the internal chamber of the conditioning module.

17. The device of claim 14, wherein the fluid inlet extends away from the conditioning module in a first direction; and
   wherein the fluid outlet extends away from the conditioning module in a second direction.

18. The device of claim 14, further comprising a sensor module disposed on the fluid inlet, the sensor module comprising one or more sensors individually configured to measure a property of fluid flowing through the fluid inlet.

19. The device of claim 18, wherein the one or more sensors comprises one or more of a pressure sensor, a temperature sensor, and an optical sensor.

20. The device of claim 14, wherein the linear portion of the flow path and the partial circumferential portion of the flow path lie in a same plane.

21. The device of claim 14, wherein the linear portion of the flow path extends along an axis that is tangential to the partial circumferential portion of the flow path.

22. A device for extracorporeal conditioning of blood, comprising:
   a conditioning module comprising an external frame, an inlet cover, an outlet cover, and defining an internal chamber;
   a first fiber assembly disposed within the internal chamber and having a first peripheral edge;
   potting material disposed throughout the first peripheral edge to create a circumferential seal that defines a passageway through the first fiber assembly having a substantially circular cross-sectional shape;
   a fluid inlet disposed on the inlet cover and defining a flow path having a first end defining a circular inlet opening and a second end adjacent the conditioning module and in fluid communication with the passageway, the second end defining a partial circumferential opening that opens to the internal chamber of the conditioning module, the flow path having a linear portion having a first internal height at the first end and a partial circumferential portion having a second internal height at the second end that is less than the first internal height; and a fluid outlet disposed on the outlet cover, the fluid outlet having an outlet lumen in fluid communication with the passageway.

23. The device of claim 22, further comprising a sensor module disposed on the fluid inlet, the sensor module comprising one or more sensors individually configured to measure a property of fluid flowing through the fluid inlet.

24. The device of claim 23, wherein the one or more sensors comprises one or more of a pressure sensor, a temperature sensor, or an optical sensor.

25. The device of claim 22, wherein the linear portion of the flow path and the partial circumferential portion of the flow path lie in a same plane.

26. The device of claim 22, wherein the linear portion of the flow path extends along an axis that is tangential to the partial circumferential portion of the flow path.

* * * * *